US011793246B2

(12) United States Patent
Trangmar et al.

(10) Patent No.: US 11,793,246 B2
(45) Date of Patent: Oct. 24, 2023

(54) BRASSIERE AND ASSOCIATED METHOD OF MANUFACTURE

(71) Applicant: VEIL INTIMATES LLC, Denver, CO (US)

(72) Inventors: Nancy Kay Trangmar, Denver, CO (US); Meghan Elizabeth Marsden, Denver, CO (US); Benjamin Elliott Stewart, Denver, CO (US)

(73) Assignee: Veil Intimates LLC, Denver, CO (US)

( * ) Notice: Subject to any disclaimer, the term of this patent is extended or adjusted under 35 U.S.C. 154(b) by 282 days.

(21) Appl. No.: 16/898,036

(22) Filed: Jun. 10, 2020

(65) Prior Publication Data

US 2020/0297043 A1 Sep. 24, 2020

Related U.S. Application Data

(63) Continuation of application No. 16/671,636, filed on Nov. 1, 2019, now Pat. No. 10,993,483, which is a continuation of application No. PCT/US2018/031428, filed on May 7, 2018, which is a continuation-in-part of application No. PCT/US2017/032026, filed on May 10, 2017.

(60) Provisional application No. 62/502,511, filed on May 5, 2017.

(51) Int. Cl.
*A41C 3/14* (2006.01)
*A41C 5/00* (2006.01)
*A61B 5/00* (2006.01)
*B33Y 80/00* (2015.01)

(52) U.S. Cl.
CPC .............. *A41C 3/142* (2013.01); *A41C 5/005* (2013.01); *A61B 5/4312* (2013.01); *A61B 5/6804* (2013.01); *B33Y 80/00* (2014.12)

(58) Field of Classification Search
CPC .... A41C 3/06; A41C 3/10; A41C 3/12; A41C 3/14
USPC ........................................... 450/39
See application file for complete search history.

(56) References Cited

U.S. PATENT DOCUMENTS

| 3,021,845 | A | * | 2/1962 | Smith | A41C 3/10 |
| | | | | | 450/39 |
| 3,446,213 | A | * | 5/1969 | Goldman | A41C 3/10 |
| | | | | | 450/39 |
| 8,840,442 | B2 | * | 9/2014 | Linkon | A41C 3/10 |
| | | | | | 450/36 |
| 2007/0026766 | A1 | * | 2/2007 | Gimble | A41C 3/12 |
| | | | | | 450/39 |

(Continued)

FOREIGN PATENT DOCUMENTS

| CN | 105235215 A | 1/2016 |
| JP | 39-8239 | 4/1939 |

(Continued)

*Primary Examiner* — Gloria M Hale
(74) *Attorney, Agent, or Firm* — Greenberg Traurig, LLP

(57) ABSTRACT

The present disclosure relates to support members for brassieres and other clothing. The support member may be manufactured by additive manufacturing, subtractive manufacturing methods, and injection molding, among others. The support member may include a thickness gradient devised to support a breast or other part of the anatomy. The support member may be customized to the anatomy of a particular user. The support member may include one or more biometric sensors.

31 Claims, 16 Drawing Sheets

(56) References Cited

U.S. PATENT DOCUMENTS

| | | | | |
|---|---|---|---|---|
| 2014/0213145 A1* | 7/2014 | McKeen | ............... | A41C 3/10 |
| | | | | 450/59 |
| 2015/0118937 A1 | 4/2015 | Wan | | |
| 2016/0044971 A1* | 2/2016 | Randall | ............... | A41C 3/142 |
| | | | | 450/39 |
| 2016/0076884 A1* | 3/2016 | Laan | ............... | G01B 21/10 |
| | | | | 702/156 |
| 2016/0183617 A1 | 6/2016 | McKinney | | |

FOREIGN PATENT DOCUMENTS

| | | |
|---|---|---|
| JP | 3107970 U | 4/2005 |
| JP | 2015-509028 A | 3/2015 |
| JP | 2015-86503 A | 5/2015 |
| WO | 2013/116242 A2 | 8/2013 |

* cited by examiner

BRASSIERE AND ASSOCIATED METHOD OF MANUFACTURE

CROSS-REFERENCE TO RELATED APPLICATIONS

This patent application is a continuation of U.S. patent application Ser. No. 16/671,636, filed Nov. 1, 2019, which is a continuation of International Patent Application No. PCT/US2018/031428, filed May 7, 2018, which is a continuation-in-part of International Patent Application No. PCT/US2017/032026, filed May 10, 2017, entitled "Formed Brassiere and Associated Method of Manufacture," which claims priority to U.S. Provisional Patent Application No. 62/502,511, filed May 5, 2017, entitled "Formed Brassiere and Associated Method of Manufacture." Priority is claimed to each of the above-identified patent applications, and each of the above-identified patent applications is incorporated herein by reference in its entirety.

BACKGROUND

Brassieres having an underwire are described in the prior art. This underwire is typically uncomfortable, drawn taught against the user's body, and points of wear exist whereby the underwire emerges from the channel at either end effectively shortening the lifespan of the brassiere.

SUMMARY OF THE INVENTION

The present invention relates to brassieres and other garments, and their associated methods of manufacture. In one approach, a brassiere or other garment having a graticulate support member disposed in between each of a first cup cover and a second cup cover. In one embodiment, a cup of the brassiere or other garment may be formable by forcing and heating to fuse the first cup cover, the graticulate support member, and the second cup cover together and effect volumetric doming of the cup particular to accommodate the anatomy of a user. The application of heat and force is sometimes referred to herein as forging. In another embodiment, the graticulate support member is originally manufactured in the appropriate size and/or shape (e.g., by additive manufacturing) and used in a brassiere or other garment. In these embodiments, the graticulate support member may be simply inserted into the garment (e.g., without being physically connected to the inner or outer cups).

Customized production of cups for particular users is likewise contemplated, whereby a scan or other image capture of a user's anatomy may render a digital image translatable to provide three dimensional imaging and production parameters of a particularly sized graticulate support member. This particularly sized graticulate support member may be, for instance, originally manufactured in the appropriate size and/shape (e.g., domical shape), or positioned between sized cup covers for volumetric doming by application of force and heat, to a particular capacity determined conformable to the particular user. Moreover, each cup of the brassiere may be individually sized and produced to produce a customized brassiere. Each cup may have its own customized graticulate support member. Aside from dome shapes, the graticulate support member may be produced in warped planes or other suitable topological members.

In one aspect, the brassiere and its associated method of manufacture enables a garment capable of supporting and uplifting one or more breasts of a user without the need of an underwire or associated channel in which such an underwire is caused to reside. The brassiere and its associated method of manufacture further enables customized cups conformed to the particular anatomy of unique users, and may enable customized garments producible upon demand.

For instance, the instant brassiere and its associated method of manufacture may include a polymer-based, additively printed (additively manufactured), graticulate support member having an arcuate first edge and an arcuate second edge. The first edge diverges from the second edge at a proximal apex, bounds a field of a graticulate matrix along one side, and converges with the second edge at a distal apex. The graticulate matrix, thus bounded by the first and second edges, comprises an angled arrangement of a plurality of interlacing members, which may define a plurality of voids of the graticulate support member. In one embodiment, a graticulate support member has a generally uniform thickness. In another embodiment, a graticulate support member has one or more selectively tailored thickness gradients.

For instance, a graticulate support member may include a maximum thickness disposed medially upon the first edge, and a minimum thickness, disposed at the second edge. A thickness gradient may be used and may be disposed from the maximum thickness at the first edge toward each of the proximal and distal apexes and the minimum thickness at the second edge. The graticulate matrix therefore may include a gradient of rigidity disposed in proportion to the thickness gradient previously described. In one embodiment, a graticulate support member has a generally uniform thickness. In another embodiment, a graticulate support member has one or more gradients of selectively tailored thickness.

The graticulate support member may be embedded between a first cup cover (e.g., an outer cup cover) and a second cup cover (e.g., an inner cup cover). A cup of a brassiere may be at least partially defined by each of the first and second cup covers with one or more graticulate support members disposed between the first and second cup covers. In one embodiment, a graticulate support member is originally manufactured in the appropriate size and/or shape (e.g., by additive manufacturing). In these embodiments, the graticulate support member may be simply inserted into the garment (e.g., without being physically connected to the inner and/or outer cups). In these embodiments, the graticulate support member may be produced as a non-planar substrate (e.g., as a domical shape). In one embodiment, the graticulate support member is originally formed as a domically shaped graticulate support member and may be readily inserted into a cup, thereby conferring the domical shape to the brassiere (e.g., to accommodate the breast of a wearer.) In another embodiment, application of heat and force is used to stretch and effect doming of the graticulate support member, thereby forming the graticulate support member and each first and second cup cover into a single volumetric cup, the graticulate support member being disposed between the first and second cup covers.

Customized volumetric cups are also contemplated, the parameters of the cups translatable from a captured image of a user's anatomy, as is described in detail below. Image capture of a particular user enables generation of a digital profile of the user. Additive printing (manufacturing) is thereby applicable to produce graticulate support members sized appropriately to meet an individual's anatomical variations. Specific sized graticulate support members may be producible from the captured image(s), such graticulate support members embedded between first (outer) and second (inner) cup covers, and one or both of the first and second cup covers may also be specifically sized based on the wearer's anatomy so as to form specific volumetric cups for a brassiere or other garment. Such customized sizing may be useful for users having anatomical variances or irregularities, e.g., as may result from postoperative surgeries, such as, for example, lumpectomies, mastectomies, augmentation, or other reconstructive, augmentative, or reductive surgeries. In embodiments where forging is used, at least a portion of a mandrel and a corresponding mold, used in forming the cups, may likewise be producible upon demand, wherein specific shaping of customized graticulate support members is affected. Thus, particular shaped cups may be created, formed and sized to the anatomy of any particular user, and producible upon demand.

The graticulate support member may be any suitable shape to facilitate support and/or uplifting of a breast or breasts of an individual. In one embodiment, a graticulate support member is of an anchor-like shape. In another embodiment, the graticulate support member is of a hook-like shape. In another embodiment, the graticulate support member is of an eye shape. In another embodiment, the graticulate support member is of a cross shape. Multiple different graticulate support members of the same shape or of multiple different shapes may be used within a single cup of a garment.

The graticulate support member may be polymer-based, and may be manufactured by any suitable methods such as, additive manufacturing, subtractive manufacturing, and/or injection molding, among others. In one embodiment, a graticulate support member is manufactured by additive manufacturing. In another embodiment, the graticulate support member is manufactured by subtractive manufacturing. In another embodiment, a graticulate support member is manufactured by injection molding.

DETAILED DESCRIPTION OF THE DRAWINGS

The present brassiere and associated method of manufacture contemplates an undergarment for women or men, wearable to support the breasts, and, as appropriate, without the need of an underwire or underwire channel. Further, the present brassiere and associated method of manufacture enables custom cups, conformable to the breasts of any particular wearer, including wearers who have undergone breast augmentation, lumpectomy, mastectomy, reconstructive surgery, or any other operation rendered to the breast capable of altering breast volume, including natural alterations resulting, for example, from pregnancy and/or breast feeding.

Figure 1:
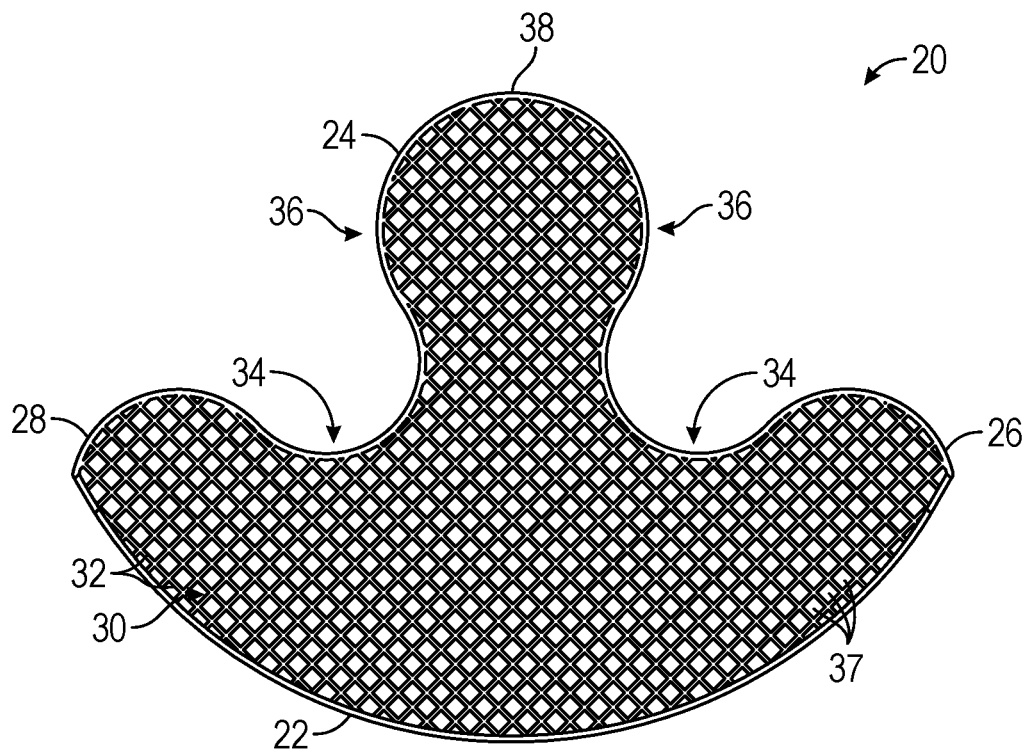
FIG. 1 is a top view of an embodiment of a graticulate support member.
Figure 2:
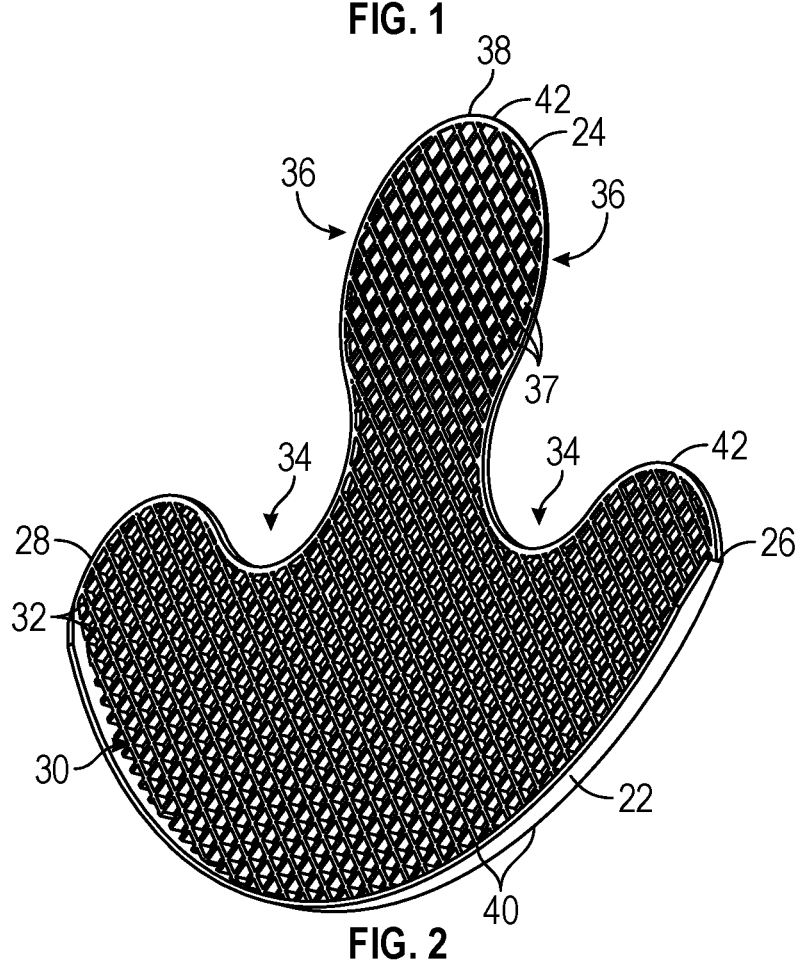
FIG. 2 is an isometric view of an embodiment of a graticulate support member.

Embodiments of a formed brassiere are described in FIGS. 1-3 and 10, where heat and/or force are used to produce formed cups. As shown in FIGS. 1-3 and 10, a formed brassiere (10) generally includes a graticulate support member (20) disposed between a first cup cover (50) and a second cup cover (52). Prior to formation of a cup (100), the graticulate support member (20) may be generally planar as shown in FIG. 1. After formation of the cup (100), the graticulate support member (20) may be dome shaped. The graticulate support member (20) includes a first edge (22) and a second edge (24). As shown in FIGS. 1-2, a graticulate matrix (30) is disposed between the first edge (22) and the second edge (24) of the support member (20). The graticulate support member (20) may further include a first (e.g., a maximum) thickness (40) realized medially at the first edge (22) and a second (e.g., a minimum) thickness (42) realized at the second edge (24). Thus, the graticulate support member (20) may generally include a graded cross-section across the graticulate matrix (30), tapering from the maximum thickness (40) toward the minimum thickness (42).

Referring now to FIGS. 3, 4A-4B, and 10, in the illustrated embodiment, the graticulate support member (20) is disposed between the first cup cover (50) and the second cup cover (52). The first edge (22) of the graticulate support member (20) provides support for the wearer underlying the breast proximal the inframammary fold, and may obviate the need of an underwire and or its associated channel. The graticulate matrix (30) may be formed to an appropriate shape so as to conform to the anatomy of a particular wearer. For instance, the second edge (24), having the minimum thickness (42), may taper inside the formed cup (100) (e.g., a breast cup) proximal the pectoralis of the wearer. Thus, the graticulate support member (20), may be disposed centrally in the cup (100), and may at least partially define the shape of the cup (100), and facilitate appropriate support for the wearer.

As noted above, the present formed brassiere (10), or other garment may be produced by additive printing (manufacturing) of the graticulate support member (20). For instance, the graticulate support member (20) may be printable, polymer-based, and shapeable between boundaries described by the first and second edges (22), (24). The graticulate support member (20) may be printed to conform to the anatomy of a particular wearer, such as adapted to an individual wearer by image capture of the particular user where the graticulate support member (20) is printable to fit a particular person.

The graticulate support member (20) may be printed as a planar substrate. The printed substrate (20) may include the maximum and minimum thicknesses (40), (42). The printed substrate (20) may be fit between the first (outer) and second (inner) cup covers (50), (52), after which the materials may be heated and fused to form a cup (100). In this regard, the materials may be heated (e.g., below the melting point or glass transition temperature of the graticulate support member (20)) to render the cup (100) formable to a desired cup shape. Doming of the cup (100) is thereby effected at the time of cup formation (e.g., when the graticulate support member (20) is inserted in between each of the first (outer) and second (inner) cup covers (50), (52) and heat is applied to form the cup shape desired). In other embodiments, the graticulate support member may be produced as a non-planar substrate, which may obviate the need to form (e.g., forge) the graticulate support member, as described in greater detail below.

The second cup cover (52) is contemplated to be a soft material (e.g., a foam), disposed to contact the breast of a wearer when the brassiere (10) is worn. The second cup cover (52) may overlie the graticulate support member (20) and remain exteriorly positioned, overlaying the breast of a wearer. Thus, while both the first cup cover (50) and the second cup cover (52) may have like doming and volumetric form (small variances in size by virtue of position relative the graticulate support member (20) notwithstanding) the second cup cover (52) may be concave relative to the support member (20), to accommodate and contact the breast of a wearer, and the first cup cover (50) may be convex to exteriorly overlie and cover the breast of a wearer.

Referring now to FIGS. 1 and 2, the illustrated graticulate support member (20) generally includes an arcuate first edge (22) and an opposite arcuate second edge (24). Each of the arcuate first and second edges (22), (24) diverge from a proximal apex (26), span the delimit of the graticulate matrix (30), and converge at a distal apex (28). The graticulate matrix (30) is disposed between the first and second edges (22), (24) in angled arrangement of interlacing members (32). The interlacing members (32) generally define a plurality of voids (37).

In the illustrated embodiment of FIGS. 1-2, the gradient of the second edge (24) is positive from the proximal apex (26), then turns negative into an inversion pocket (34), before turning positive again to rise through an S-shaped portion (36), to culminate at an apical arc (38) at a distance farthest from the first edge (22). The second edge (22) maintains symmetry reflected through a medial axis of the graticulate support member (20), and defines a like perimeter between the apical arc (38) and the distal apex (28).

Figure 6:
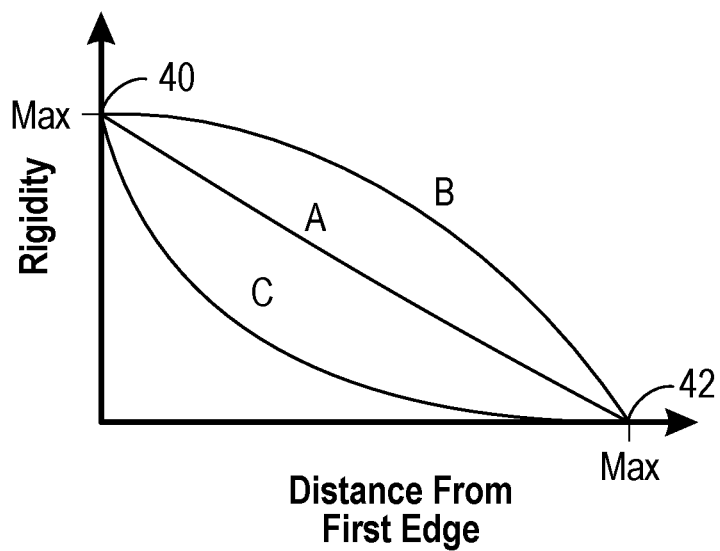
FIG. 6 is a graphical representation of example gradients of rigidity from a first edge of a graticulate support member to a second edge of a graticulate support member.

As shown in FIGS. 1 and 2, a maximum thickness (40) may be realized medially at the first edge (22) and a minimum thickness (42) may be realized at the second edge (24). The cross-section of the graticulate support member (20) may therefore taper from the maximum thickness (40) to the minimum thickness (42), from the first edge (22) toward the second edge (24) and toward each of the proximal and distal apexes (26), (28). In this regard, a decrease in rigidity may be realized between the maximum thickness (40) and the minimum thickness (42) (e.g., as illustrated in FIG. 6). The first edge (22) may be maximally rigid at a medial point, relative to the second edge (24), in which the second edge (24) may be minimally rigid. Deformation of the graticulate support member (20) may thus be effected by applying controlled force and heat thereto, the force distributed through the graticulate matrix (30) between the maximum thickness (40) and the minimum thickness (42).

In other embodiments, a graticulate support member (20) may be originally produced as a non-planar substrate. In one embodiment, a non-planar graticulate support member is produced as a net-shape product or a near-net shape product, wherein its final product form is achieved during its production (e.g., by additive manufacturing, by injection molding). Such graticulate support members may be utilized, for instance, as replaceable components of a garment (e.g., a brassiere cup). In such applications, the graticulate support member may be originally produced with the appropriate size and shape for the garment (e.g., to accommodate the breast of a wearer when used in a brassiere), thereby obviating the need for the application of force and/or heat to impart the domical shape. Thus, in one embodiment, a cup is produced using a non-planar graticulate support member and at least one of an inner cup and an outer cup, and in the absence of deformation of the non-planar graticulate support member.

Figure 5:
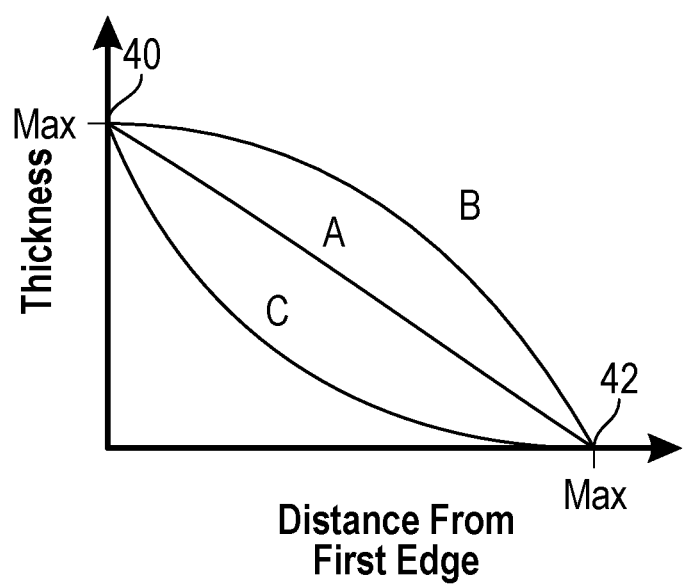
FIG. 5 is a graphical representation of example gradients of thickness from a first edge of a graticulate support member to a second edge of a graticulate support member.

FIGS. 5 and 6 illustrate graphical representations of embodiments associated thickness profiles (FIG. 5) and corresponding rigidity profiles (FIG. 6). Maximum thickness (40) tapers along a gradient (gradients A, B, or C are shown as examples of thickness curves) in proportion to distance from a medial point disposed upon the first edge (22), as shown in FIG. 5. Likewise, as shown in FIG. 6, rigidity tapers along a gradient (gradients A, B, or C are shown as examples of rigidity curves) in proportion to distance from the medial point disposed upon the first edge (22).

Figure 7:
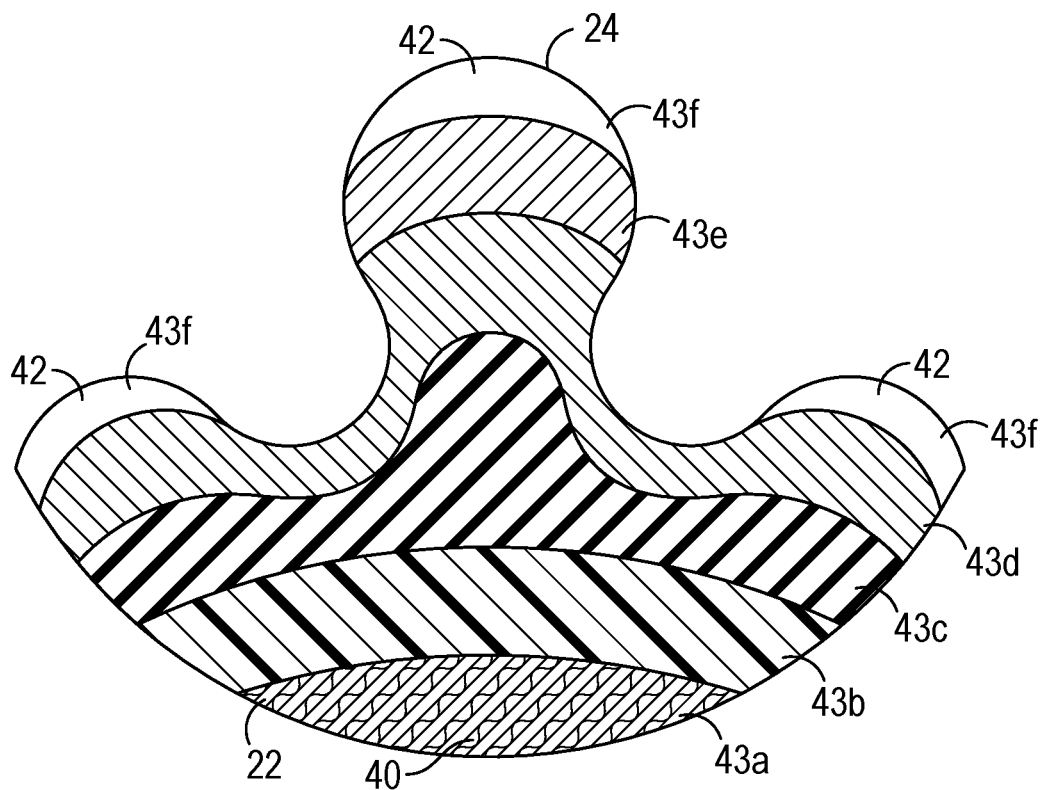
FIG. 7 is a top view of a graticulate support member having a variable thickness graticulate matrix disposed between its first and second edges.

FIG. 7, illustrates one embodiment of a support member (20) having discrete sections of variable thickness. The maximum thickness (40) is located along the first edge (22) and has a maximum thickness (43a). The gradient tapers from the maximum thickness section (43a) to the minimum thickness section (43f). The first section (43a) comprises a maximum thickness and the sixth section (43f) comprises a minimum thickness. The second (43b), third (43c), forth (43d) and fifth (43e) sections may each have different thickness from each other and from the first (43*a*) and sixth (43*f*) sections. The thickness decreases in each intermediate section (43*b*-43*d*) may be monotonic.

As illustrated, the new support members (20) may include a maximum thickness (e.g., along a first edge (22)), and a minimum thickness (e.g., along a second edge (24)). In these embodiments, a thickness gradient may exist between the maximum thickness and minimum thickness of the support member (20). In one approach, the gradient may comprise one or more sections of variable thickness between the maximum thickness and minimum thickness. Additionally, the gradient may be a monotonic gradient (i.e. strictly decreasing from the maximum thickness to minimum thickness) or a non-monotonic gradient. Furthermore, the gradient may be a uniform (e.g., linear) or a non-uniform gradient. In one embodiment, the gradient between the maximum thickness and minimum thickness is a continuous gradient. In another embodiment, the gradient between the maximum thickness and minimum thickness is a discrete gradient, containing one or more sections of variable thickness between the maximum thickness and minimum thickness. In one embodiment, the gradient may be linear and monotonic. In another embodiment, the gradient may be non-linear and monotonic. In another embodiment, the gradient may be non-linear and non-monotonic. As stated above, a thickness gradients may produce a support member (20) having a rigidity gradient, wherein the rigidity gradient is generally in proportion to the thickness gradient.

Figure 15:
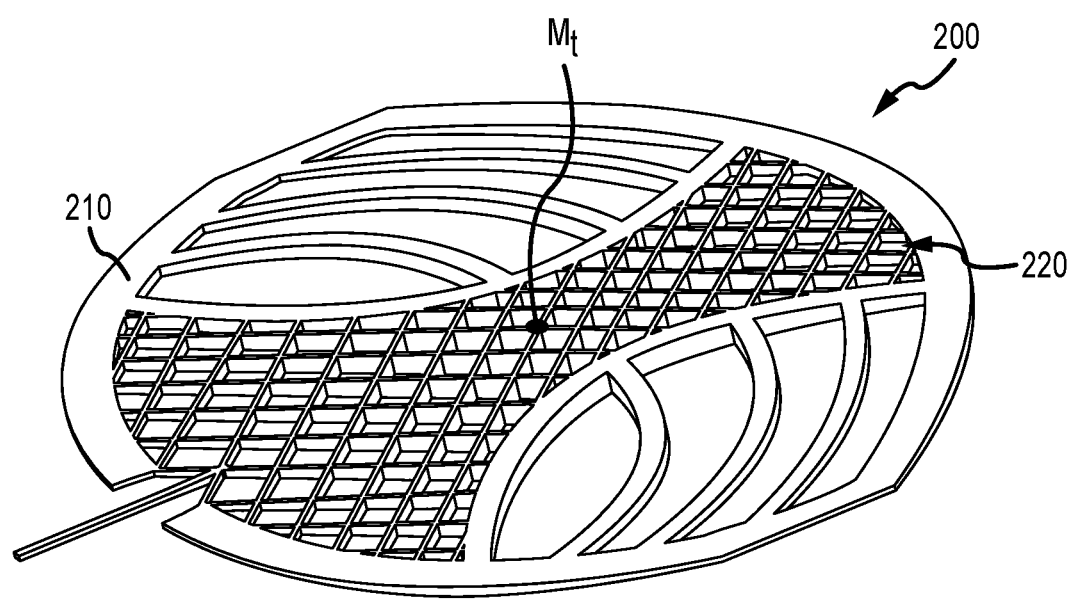
FIG. 15 is a perspective view of an embodiment of the graticulate support member wherein the thickness of the graticulate support member radially decreases from a central location.

In one embodiment, and referring now to FIG. 15, a graticulate support member (200) may comprise a maximum thickness ($M_t$) proximal a center region of a graticulate matrix portion (220). (FIGS. 16*a*-16*c*, below, describe additional structure associated with the illustrated embodiment.) In one embodiment, a thickness gradient is employed wherein the thickness of the graticulate support member (200) decreases with increasing distance from the central maxima ($M_t$). In one embodiment, the thickness decrease is continuous and/or uniform. In another embodiment, the thickness decrease is non-continuous and/or non-uniform (e.g., discrete decreases; stepped decreases). In one embodiment, a thickness decrease is linear. In another embodiment, a thickness decrease is non-linear (e.g., a polynomial decrease; an exponential decrease; a logarithmic decrease). In one embodiment, another portion of the graticulate support member (200) comprises a minimum thickness ($L_t$) (not illustrated). In one embodiment, the minimum thickness may be associated with the outer perimeter (210). In one embodiment, the ratio of $L_t$ to $M_t$ is not greater than 0.90, or not greater than 0.75, or not greater than 0.60 or not greater than 0.50, or not greater than 0.40, or not greater than 0.35, or not greater than 0.30, or not greater than 0.25, or less. In other embodiments (not shown), the minimum thickness location ($L_t$) and the maximum thickness location ($M_t$) may be switched, wherein the maximum thickness ($M_t$) is associated with an outer perimeter (210) of the graticulate support member, and wherein the minimum thickness ($L_t$) is associated with the graticulate matrix portion (220). Any of the thickness approaches described herein can be used with any of the graticulate support members described or illustrated herein.

In one embodiment, and with continued reference to FIG. 15, a radial thickness gradient may be used wherein the thickness of the graticulate support member (200) decreases generally uniformly, and in every direction, with increasing distance from the maximum thickness ($M_t$) location. A radial thickness gradient may be useful in, for instance, facilitating an appropriate distribution of a user's weight (e.g., distributing the weight of a breast in a brassiere).

Figure 3:
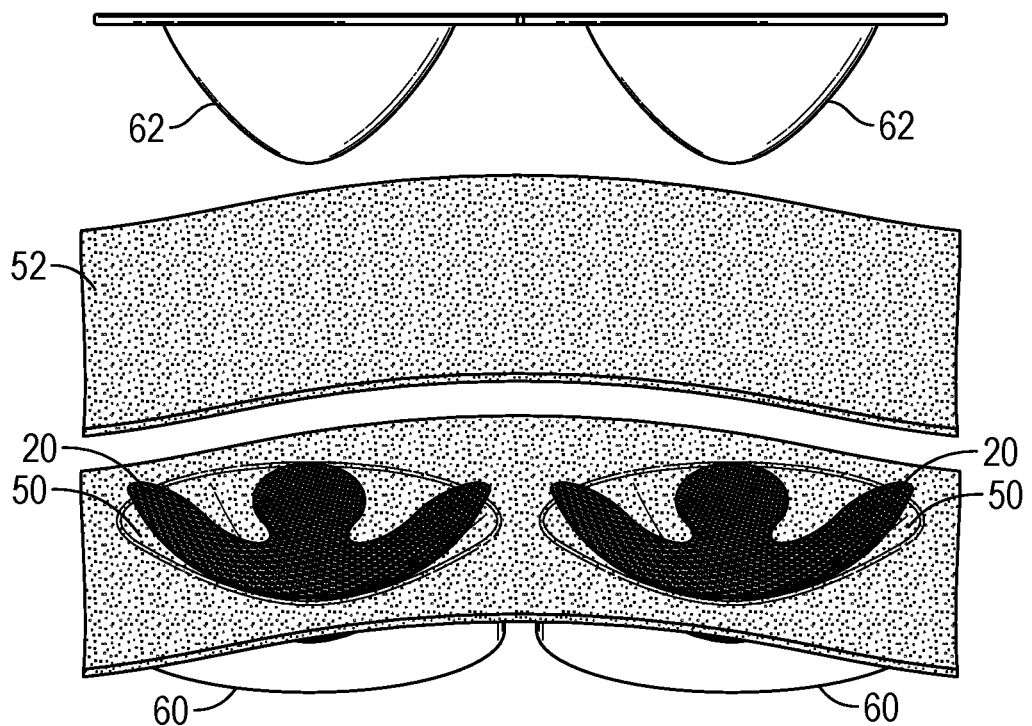
FIG. 3 is an elevation view of an embodiment of a formed brassiere about to be pressed showing the graticulate support member disposed atop a first cup cover.

When forming operations are used, and referring now to FIG. 3, a first cup cover (50) may be disposed to underlie the graticulate support member (20) and a second cup cover (52) may be disposed to overlie the graticulate support member (20). Once positioned appropriately, a cup (100) may be formable by application of heat and force to mold the cup (100) to the desired shape and fuse the graticulate support member (20) and first (outer) and second (inner) cup covers (50), (52) into a single cup (100). The graticulate support member may be fused to one of or both of the first and second cup covers. Thus, cups (100) are formable to a desired shape, and a brassiere (10) is thereby realized for wear.

Figure 4A:
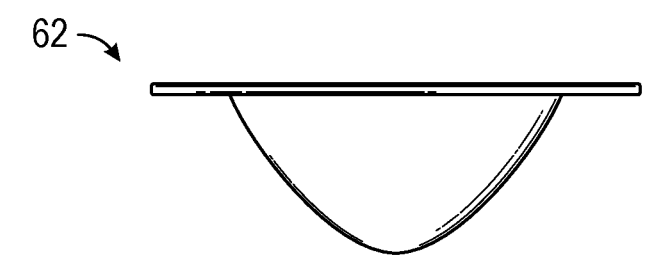
FIG. 4A is an elevation view of a cup formed domically whereby the graticulate support member interior to the cup maintains shape of the cup and each of the associated first and second cup covers are cohesive thereby.
Figure 4A:
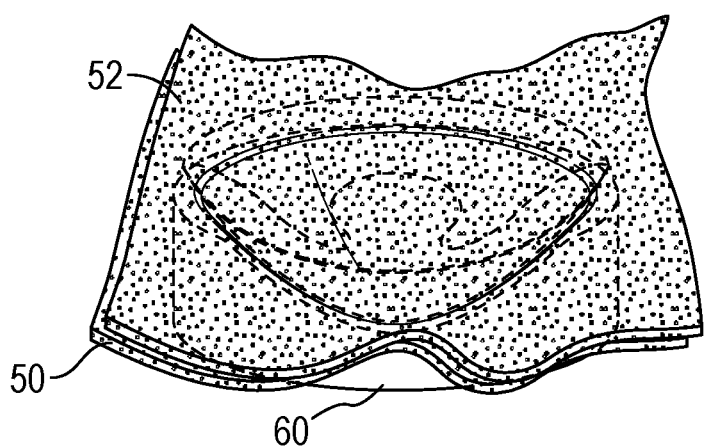
Figure 4B:
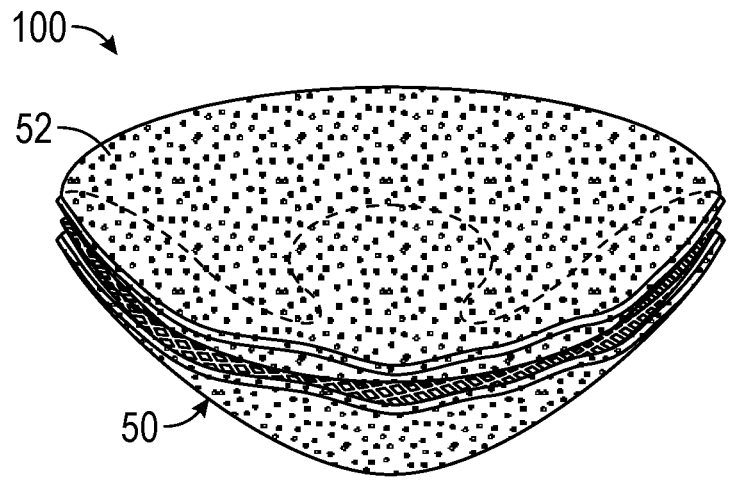
FIG. 4B is an elevation view of a cup formed domically with the graticulate support member therein.

When forming operations are used, and referring now to FIGS. 3, 4A, and 4B, a mandrel (62) may be used to force doming of the cups (100) by action of force and heat applied below the melting point (crystalline and semi-crystalline polymers) or glass transition temperature (amorphous polymers) of the graticulate support member (20). A mandrel (62) may apply force to effect doming of the graticulate support member into a mold (60) whereby domic shaping of the cups (100) is facilitated. The graticulate support member (20) may thus fuse the first (outer) and second (inner) cup covers (50), (52) together, and may maintain the specific shape produced by forcing of the mandrel (62) into the mold (60) at temperature.

Figure 8:
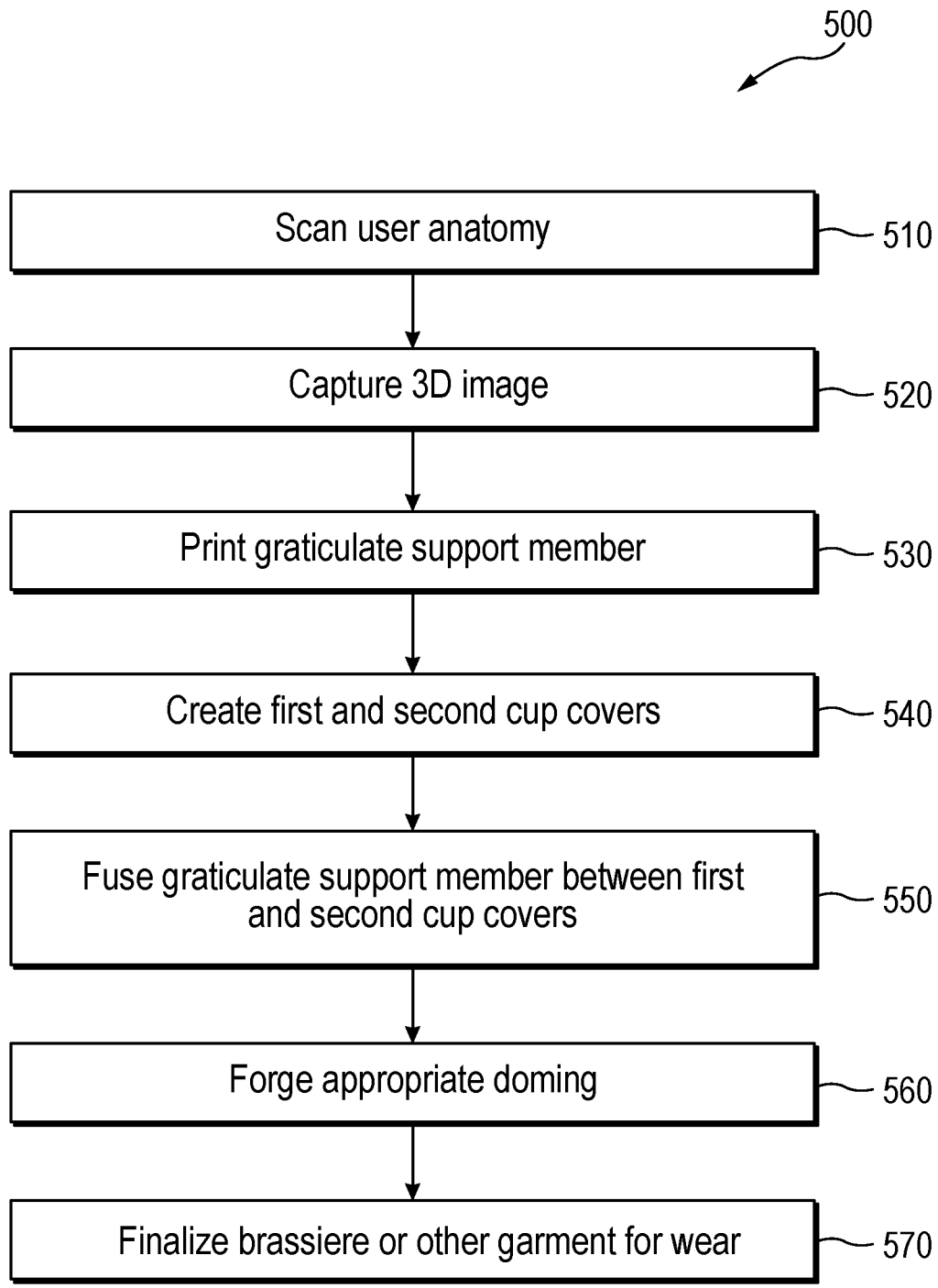
FIG. 8 is a flow diagram of an example method of manufacture of one or more formed cups to create a customized formed brassiere for wear by a particular user.

Referring now to FIG. 8, one embodiment of a method for producing a brassiere or other garment (500) having an enclosed customized support member is illustrated. As described above, formation of one or more particular cups devised for wear by a particular user to accommodate a unique anatomy, may be producible by utilizing image capture of a particular user's anatomy. For instance, a user may have one or more portions of their anatomy scanned (510), for instance, by utilizing a digital (or analog) camera, or multiple digital (or analog) cameras. The scan may be used to capture a 3D image (520) of the user's anatomy. The 3D image may be used to determine a user's anatomical features, wherein a customized support member may be printed (additively manufactured) (530) to accommodate a user's specific anatomical features. For instance, an anatomical feature may be the weight distribution of a user's breast(s). A weight distribution of a user's breast(s) may be accommodated, for instance, by manufacturing a support member (20) with a custom gradient, where regions of the support member (20) may have increased thickness to accommodate regions of higher weight distribution of a breast. In one embodiment, cups may be formed by creating the first and second cup covers (540), fusing the custom support member between the first and second cup covers (550), then forging (560) one or more cups. The cups may be fitted to brassiere or other garment components (e.g., straps, wings, bands, and a bridge) to finalize a brassiere or other garment for a wearer.

Figure 9:
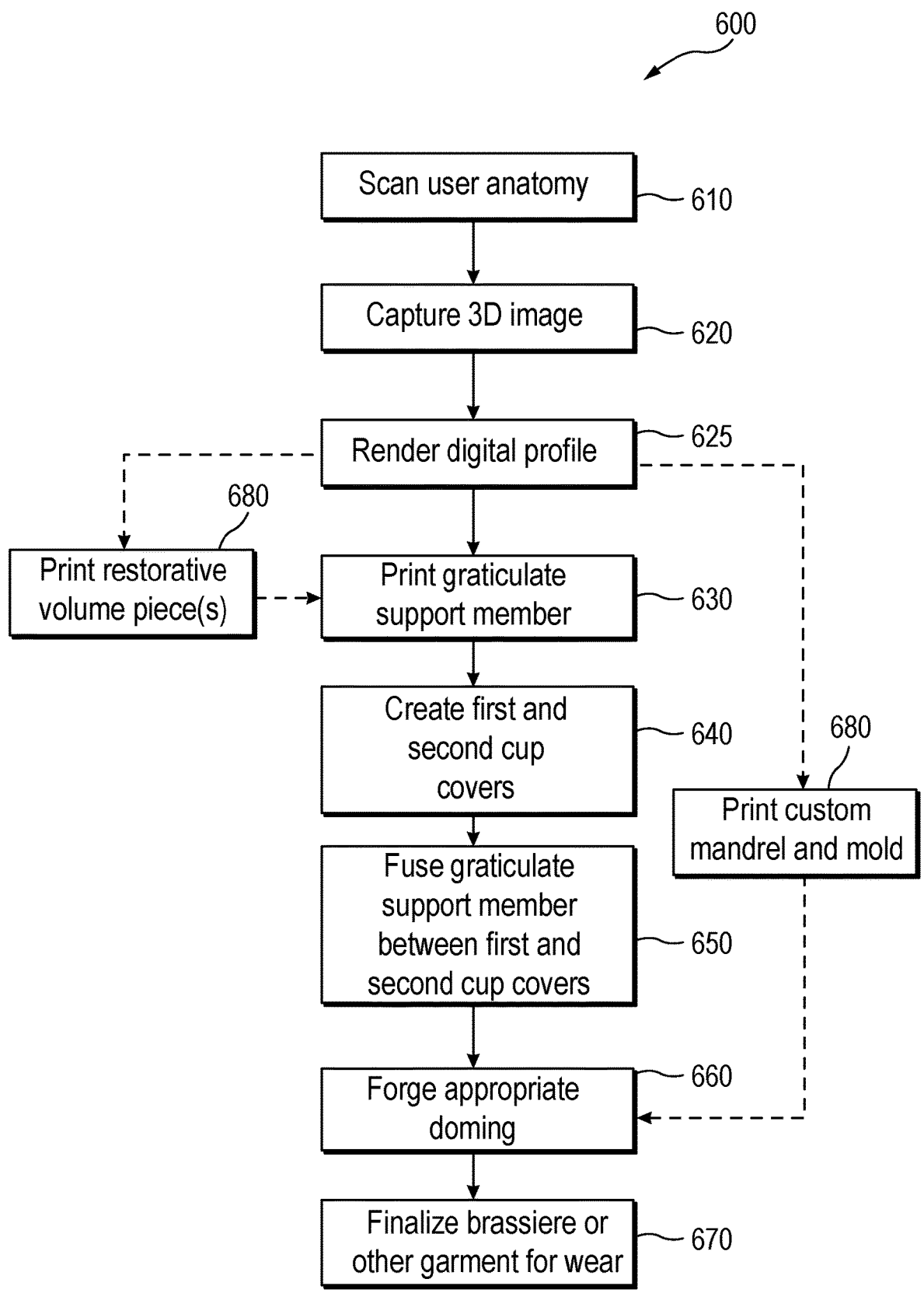
FIG. 9 is a flow diagram of an example method of manufacture of one or more formed cups to create a customized formed brassiere for wear by a particular user.

Referring now to FIG. 9, one embodiment of a method for producing a brassiere or other garment (600) having an enclosed custom support member (20) is illustrated. As described above, production of particular cups devised for wear by a particular user to accommodate a unique anatomy, may be producible by utilizing image capture of a particular user's anatomy. For instance, a user may have their anatomy scanned (510), for instance, by utilizing a digital (or analog) camera, or multiple digital (or analog) cameras. The scan may be used to capture a 3D image (520) of one or more portions of the user's anatomy. A digital profile of a user may then be rendered (625). A digital profile may comprise the data of the 3D measurements of an altered breast, portions of a breast removed by an operation, and completely removed breasts removed by an operation, among others. For instance, a digital profile of a breast may be of a breast removed by a mastectomy procedure, or portions removed by a lumpectomy. As described in greater detail below, a digital profile may be utilized to produce a restorative volume piece (e.g., prosthetic) or pieces (627), which may be manufactured to fill the negative volume created by a breast operation. A restorative volume piece or pieces may be additively manufactured using a suitable material, as described in greater detail below. The restorative volume piece or pieces may be manufactured separately, to be later stitched into a breast cup, enclosed between a first cup cover and second cup cover, or printed onto a support member to be enclosed between a first cup cover and a second cup cover, among others. A support member may be printed (630) utilizing the digital profile. As described in greater detail below, a restorative volume piece or pieces may be incorporated into the support member, wherein the support member acts as a substrate for the piece(s). First and second cup covers may be created (640). When a forging operation is used, the custom support member and or restorative volume piece(s) may utilize an optional custom mandrel and corresponding mold. As described in greater detail below, a custom mandrel and corresponding mold may be produced by printing (additively manufacturing) the mandrel and mold (680). In one embodiment, one or more cups are formed by inserting the graticulate support member into a brassiere. When a forging operation is used, one or more cups may be formed by fusing (650) the support member, optionally a restorative volume piece or pieces, between the first and second cup covers, then forging (660) to create the one or more cups. The one or more cups may be fitted to a brassiere or other garment components (e.g., straps, wings, bands, and a bridge) to finalize a brassiere or other garment for a wearer. The forging step (660) may optionally comprise utilizing a custom mandrel and corresponding mold.

Still referring to FIGS. 8 and 9, formation of particular cups devised for wear by a particular user, and shaped, therefore, to accommodate a unique anatomy is contemplated by image capture of the particular user's anatomy. Image capture of the particular user's anatomy enables three dimensional modeling of the user's anatomy as a digital profile, whereby additive printing of customized graticulate support members is facilitated. Appropriately sized graticulate support members are thereby printable by additive printing from a suitable polymer-based material. Like the graticulate support members, the first (outer) and/or second (inner) cup covers may be produced (e.g., stamped from foam blanks; additively manufactured). When forging is used, one or more cups are then formable to dome volumetrically and fuse the graticulate support member interior the cup, between the first (outer) and second (inner) cup covers. One or more cups may be fitted to straps and blanks and a brassiere or other garment is thus realizable for a particular user upon demand.

When forging is used, the mandrels themselves may be additively manufactured or otherwise customized and produced. In one embodiment, at least a portion of the mandrel, such as an outer covering, for example, may be producible on demand in representation of a particular user's anatomy, for example, to accommodate irregular shaped breasts as may result from post-operative procedures, such as lumpectomies and partial mastectomies. In a like manner, at least a portion of the mold, such as an outer covering, for example, may also be producible on demand in representation of a particular user's anatomy.

Figure 10:
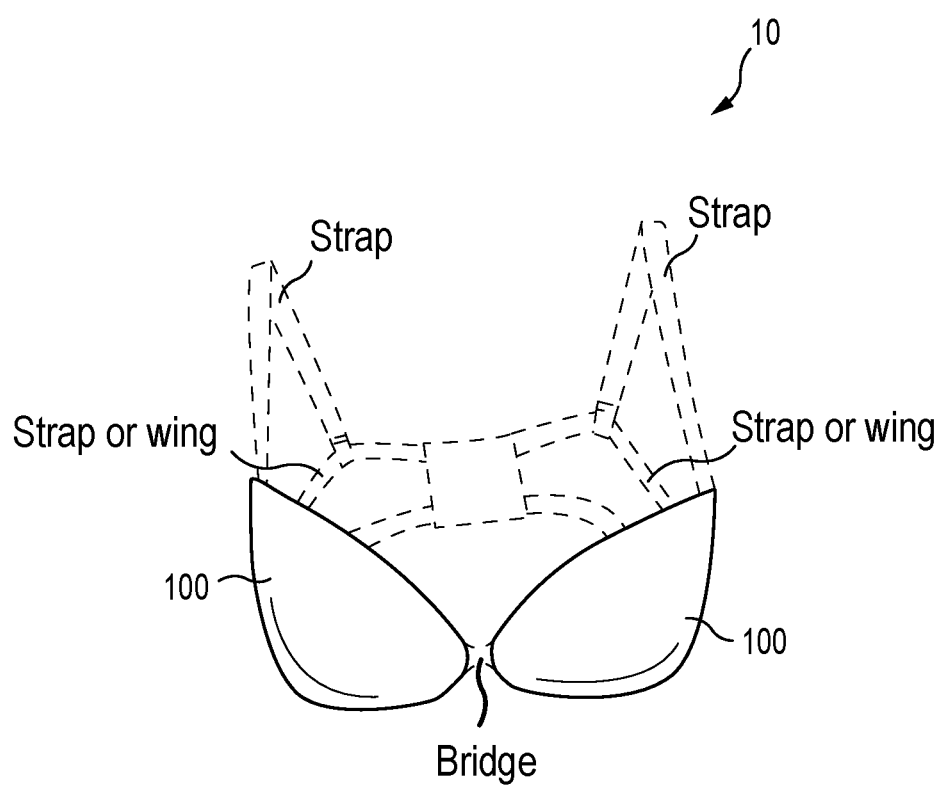
FIG. 10 is an embodiment of a formed brassiere, wherein one or more of the cups include a graticulate support member therein.

Referring now to FIG. 10, a brassiere (10) or other garment may comprise fitting the cups (100) with additional components. For instance, as illustrated in FIG. 10, a brassiere (10) may further comprise one or more straps, one or more wings, and one or more bridges. The bridge (or other connector) may be used to connect a first cup (100) adjacent to a second cup (100). Zipper(s) and/or Velcro may also or alternatively be used to connect the cups. Additionally, components not shown in FIG. 10 may include bands (e.g., a compression band for post-surgical wear). As may be appreciated, a brassiere or other garment (10) may comprise a single cup (100) comprising a polymer-based graticulate support member disposed between an inner cup cover, and an outer cup cover. The inner cup cover and the outer cup cover may define a pocket for the graticulate support member. In another embodiment, at least one of the inner cup cover and the outer cup cover are forged with the graticulate support member to form the final cup shape. The brassiere or other garment (10) may further comprise a second cup (100) having a second inner cup cover, and a second outer cup cover. In some embodiments, the second cup (100) comprises a second polymer-based graticulate support member disposed between the second inner cup and the second outer cup. As above, a pocket can be used for the second graticulate support member or the second graticulate support member may be forged with the inner cup and/or outer cup. In other embodiments, the second cup is absent of any graticulate support member. As described below in further detail, a brassiere (10) or other garment may comprise various combinations of a first cup design and a second cup design, wherein at least one of the first cup or second cup comprise an enclosed support member.

While the above embodiments generally relate to brassieres absent of an underwire, the new support members (20) described herein may also be employed with wired brassieres and or other wired clothing (e.g., for addition support and or modesty enhancement as described in further detail below).

While the above embodiments generally relate to enclosing a single support member (20) in a breast cup (100), it may be appreciated that at least two support members (20) may be enclosed into a breast cup (100) to realize support of an individual's breast(s), as well as enhancing modesty, among others.

Types of Clothing

As described above, the new support members (20) may be used with brassieres and other applicable garments. For instance, the new support members (20) may be used in intimate apparel, evening wear, swimwear, activewear (e.g., sportswear and athleisure wear), post-surgical apparel, maternity wear, bridal wear, and defense wear, among others. The support members (20) may be used for aesthetic apparel (e.g., having more aesthetic qualities than functional qualities), for instance, in intimate apparel, evening wear, and bridal wear, among others. Alternatively, the support members may be used for functional apparel (e.g., having more functional qualities than aesthetic qualities), for instance, in activewear, and swimwear, among others. Non-limiting examples of intimate apparel include lingerie, nightgowns, brassieres, and shapewear. Non-limiting examples of evening wear including strapless brassieres, balconette brassieres, plunge brassieres, bralettes, bodysuits, and lingerie. Non-limiting examples of swimwear include bikini tops, wetsuits, drysuits, one-piece swimsuits, swim dresses, and tankini tops. Non-limiting examples of activewear include workout brassieres, sports brassieres, and workout tops (e.g., tank tops, t-shirts, long-sleeve shirts). Non-limiting examples of post-surgical apparel include brassieres having an implant stabilizer band, and compressive brassieres (e.g., to enhance recovery). Transitional apparel includes brassieres intended for use by a wearer who may be transitioning from post-breast(s) surgery (e.g., augmentation, lumpectomy, mastectomy, and double-mastectomy) to reconstruction. One non-limiting example of transitioning apparel is a compressive brassiere. Non-limiting examples of maternity wear include nursing brassieres and maternity brassieres. Non-limiting examples of bridal wear include bustiers, bridal bodysuits, gowns, and corsets. Non-limiting examples of defense wear includes body armor (e.g., bullet-proof clothing).

Enhanced Modesty

Aside from providing support for the breast(s) of a wearer, the new support members (20) may facilitate enhanced modesty garments. As illustrated in FIG. 3, the support member (20) is located between the first and second cup covers (50), (52). As may be appreciated, the areola and/or nipple of a breast are generally situated toward the middle of the support member. Thus, the support member (20) may overlay the areola and/or nipple area of a breast, thereby masking of unwanted highlighting of these regions while the garment is being worn. In other words, an incorporated support member (20) may distribute the force exerted by an areola and/or nipple over the area comprising the support member (20), therefore resulting in masking of unwanted highlighting of an areola and/or nipple.

Manufacturing of the Support Member

As described above, the new support members (20) may be manufactured by additive manufacturing, among other methods. As used herein, "additive manufacturing" means, "a process of joining materials to make objects from 3D model data, usually layer upon layer, as opposed to subtractive manufacturing methodologies", as defined in ASTM F2792-12a entitled "Standard Terminology for Additively Manufacturing Technologies". In one embodiment, an additive manufacturing process comprises utilizing Continuous Liquid Interphase Printing ("CLIP"), such as in the methods described in U.S. Pat. No. 9,360,757, entitled, "Continuous Liquid Interphase Printing," the disclosure of which is incorporated herein by reference in its entirety.

Generally, the new support members (20) are manufactured using a polymer-based material. Polymer-based materials may be thermoplastics, elastomers, or thermoplastic elastomers. The polymer-based material may also be a combination of an elastomer material and a thermoplastic material, which may be considered a thermoplastic elastomer. Thermoplastic elastomers may be, for instance, formed by physical mixing of a thermoplastic and an elastomer, or through creation of chemical bonds between a thermoplastic material and an elastomer material, and combinations thereof. Non-limiting examples of thermoplastics include polypropylene, acrylonitrile-butadiene-styrene (ABS), polystyrene, polyvinyl chloride, polylactic acid (PLA), polyethylene terephthalate (PET), polyether imides, nylons, polycarbonates, polyacrylonitrile, and combinations thereof. Non-limiting examples of elastomers may be polyisoprene, polybutadiene, chloroprene, butyl rubber, silicone rubber, chlorosulfonated polyethylene, fluoroelastomers (e.g., viton), and combinations thereof. A thermoplastic elastomer may be formed, as described above, by physical mixing or chemical bond formation, between at least one of any of the above thermoplastics, and at least one of any of the above elastomers.

A suitable material for manufacturing the new support members (20) may have specific properties or qualities. For instance, the material may comprise a polymer or mixture of polymers which are formable, flexible, yet strong enough to support breasts. Additionally, the material may comprise a polymer or mixture of polymers which react well to different temperatures. For instance, forming a cup (100) may comprise subjecting the materials to a temperature greater than 400° F. during the forging step. A suitable material may, therefore, have a melting temperature (e.g., for semi-crystalline or crystalline polymers) or a glass transition temperature (e.g., for an amorphous polymer) of at least 400° F. (204° C.) and above the forging temperature. The support member material may be compatible with commercial or residential clothing washing and drying operations. Commercial or residential washing and drying operations may include conditions of elevated temperatures, exposure to water, exposure to soaps, and exposure to bleach, of which the support member material may be resistant. Further, a commercial or residential clothing dryer may attain temperatures not greater than 200° F. (93° C.), thus the material may retain its shape memory characteristics up to 200° F. (93° C.).

In one embodiment, the new support members (20) comprise a polymer or mixture of polymers with a melting temperature or glass transition temperature of at least 500° F. (260° C.). In another embodiment, the new support members (20) comprise a polymer or mixture of polymers with a melting temperature or glass transition temperature of at least 600° F. (316° C.). In another embodiment, the new support members (20) comprise a polymer or mixture of polymers with a melting temperature or glass transition temperature of at least 700° F. (371° C.).

In one embodiment, the new support members (20) are manufactured from a thermoplastic. In another embodiment, the new support members (20) are manufactured from an elastomer. In another embodiment, the new support members (20) are manufactured from a thermoplastic elastomer. In one embodiment, the new support members (20) are manufactured from a thermoplastic elastomer comprising Nylon-6. In another embodiment, the new support members (20) are manufactured from a thermoplastic elastomer comprising polyurethane. In another embodiment, the new support members (20) are manufactured from a thermoplastic comprising Nylon-6. In another embodiment, the new support members (20) are manufactured from a thermoplastic comprising polyurethane.

In addition to producing the new support members (20) by additive manufacturing, the new support members (20) may be manufactured by subtractive manufacturing. For instance, a subtractive manufacturing method suitable for production of the new support members (20) may be CNC (computer numerical control) machining. CNC machining comprises utilizing a computer to control machining tools to fabricate a product. A CNC machine may carry out an array of operations such as cutting, carving, milling, drilling, laser cutting, among others, on a precursor material, thereby subtracting portions to form a product. CNC machining may include utilizing 3D model data, which may allow a manufacturer the flexibility of producing customizable support members (20) for brassieres and garments. As another example, injection molding (e.g., rapid injection molding) may be used to produce the new support members (20), where, for instance, injection molding may be suitable for the production of new support members (20) not requiring customization (e.g., a support member for a commercial brassiere or garment).

As described above, the new support members (20) may include a graticulate matrix (30) comprising an angled arrangement of interlacing members (32), which define a plurality of voids (37), as seen in FIG. 1. The interlacing members (32) may produce voids (37) of various shapes. As illustrated, the interlacing members create a square or rectangular pattern. In other embodiments, at least some of the interlacing members may be non-perpendicular, creating a parallelogram or rhombus pattern. Indeed, any suitable arrangement of the interlacing members may be used. In one embodiment, the interlacing members are generally linear, as illustrated in FIG. 1. However, the interlacing members may be non-linear, comprising one or more curves/arcuate portions. The voids defined thereby may thus be of any suitable shape, including rectangular, rhombus, oval, circular, ellipsoidal, triangular, honeycomb-like eye-shaped or otherwise. Further, one or more of the interlacing members may be of a uniform thickness, or may be of a varied thickness. Similarly, one or more the interlacing members may be of a uniform width or may be of a varied width (see, e.g., FIG. 17). Likewise, one or more of the interlacing members may be of a uniform length, or may be of a varied length.

Figure 11A:
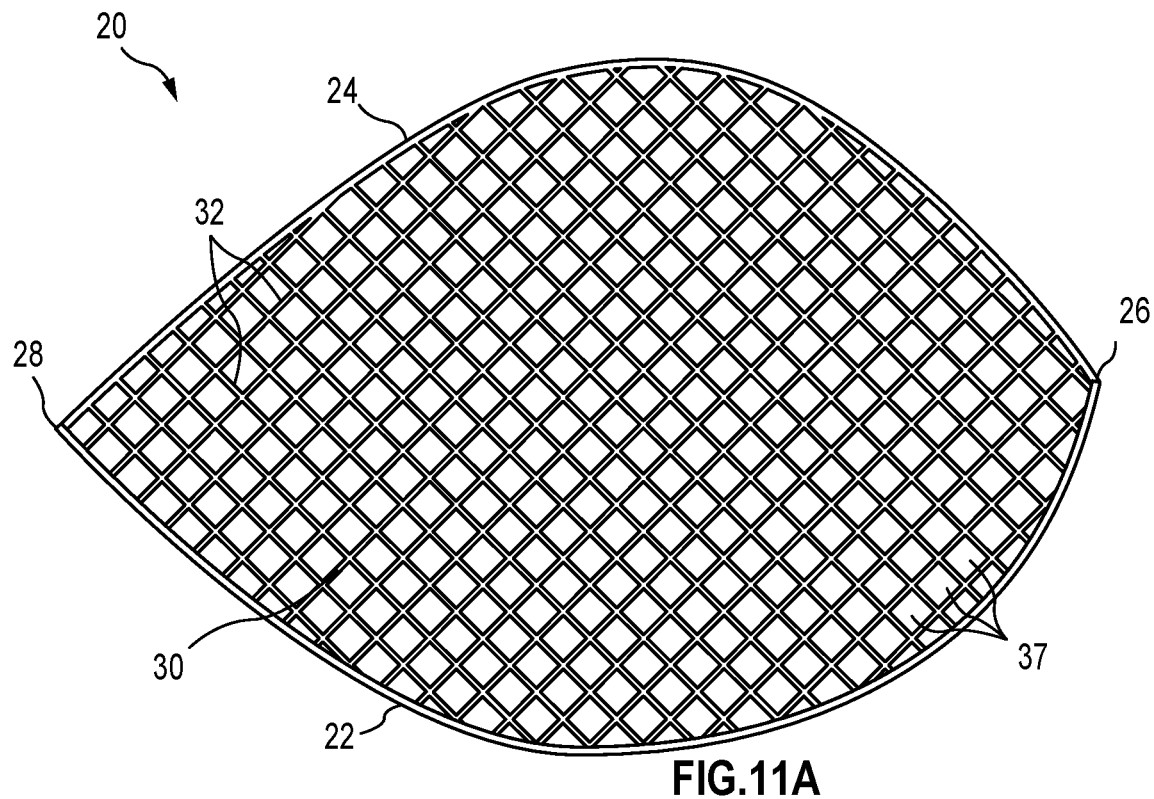
FIG. 11A is a top view of an embodiment of a graticulate support member in the shape of an eye.
Figure 11B:
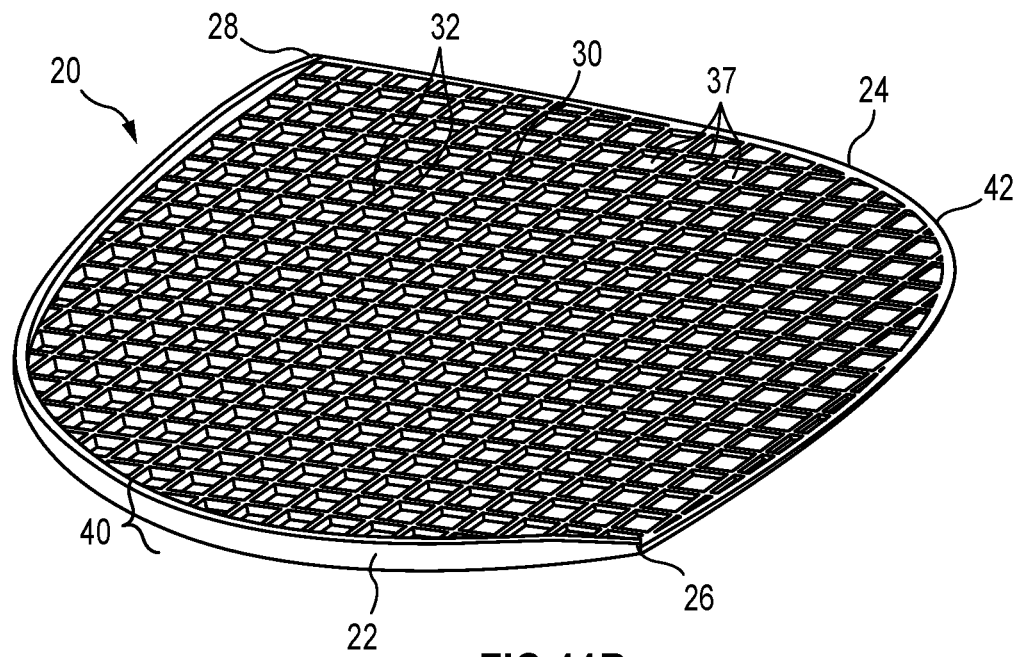
FIG. 11B is an isometric view of the graticulate support member of FIG. 11A.
Figure 12:
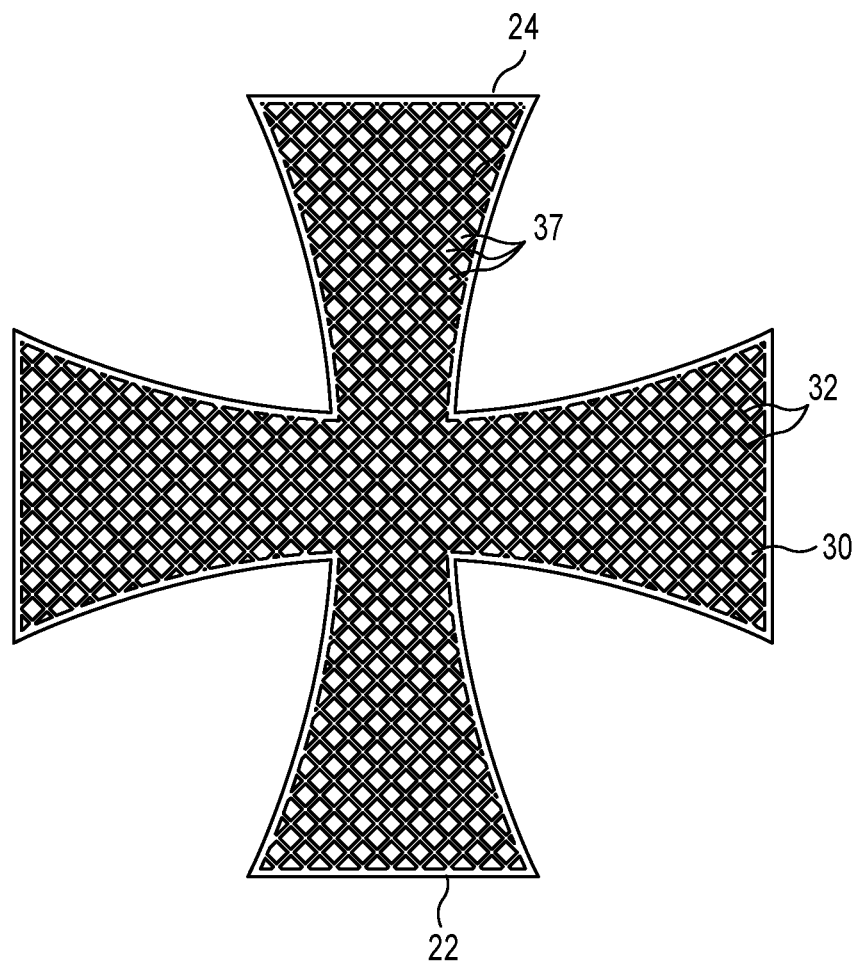
FIG. 12 is a top view of an embodiment of a graticulate support member in the shape of a cross.

A support member may be of any suitable shape. In one embodiment, the support member (20), may facilitate a breast cup (100) having a smooth inner and outer surface (e.g., the support member does not fold and a support member is an anchor-like shape, as shown in FIG. 1 and FIG. 2. Another example of a support member shape may be an eye shape, as shown in FIGS. 11A and 11B. Yet another example of a support member shape may resemble a symmetrical, cross, having arms of equal length, which broaden from the center non-linearly, as seen in FIG. 12. In another embodiment, a support member is of a hook shape.

Figure 16A:
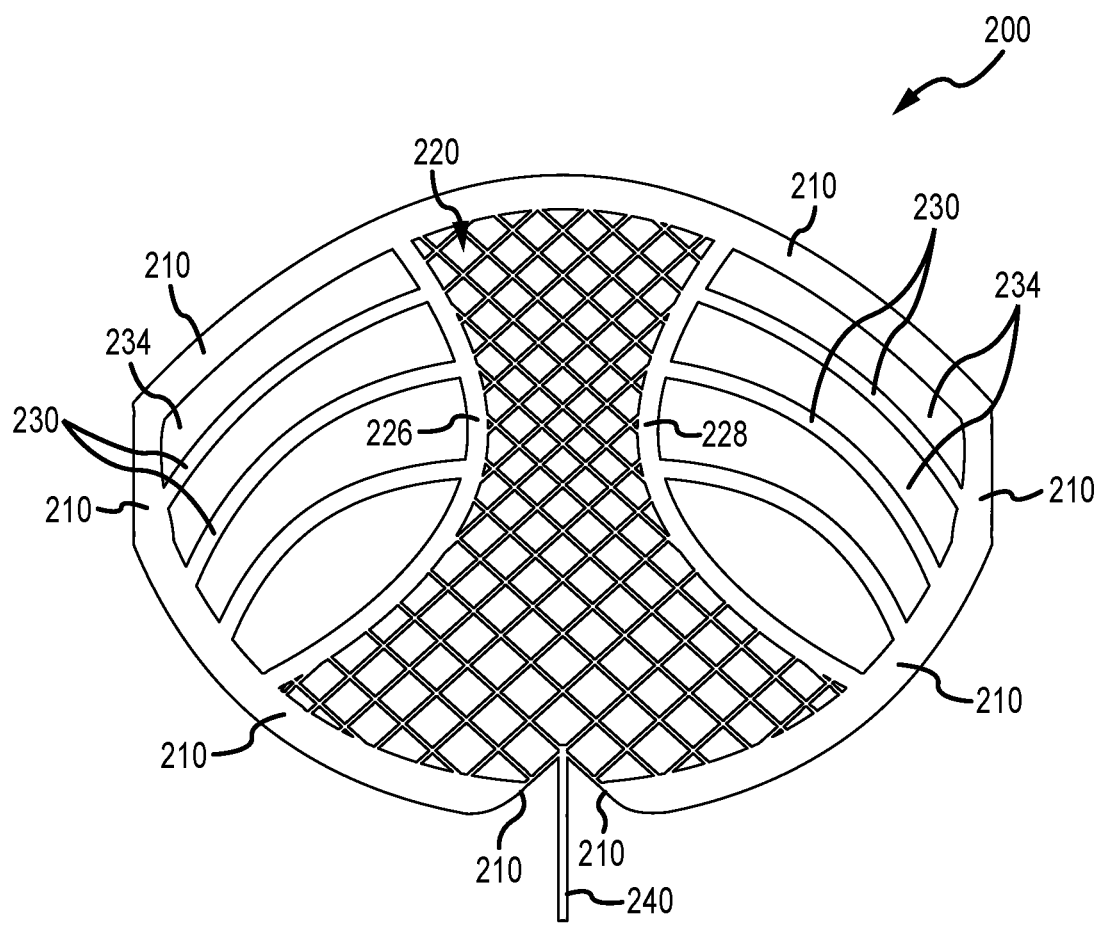
FIGS. 16a-16c are top views of one embodiment of graticulate support member having an inner graticulate support matrix portion with a plurality of arms extending between the outer perimeter of the graticulate support member and the inner graticulate support matrix portion.
Figure 16B:
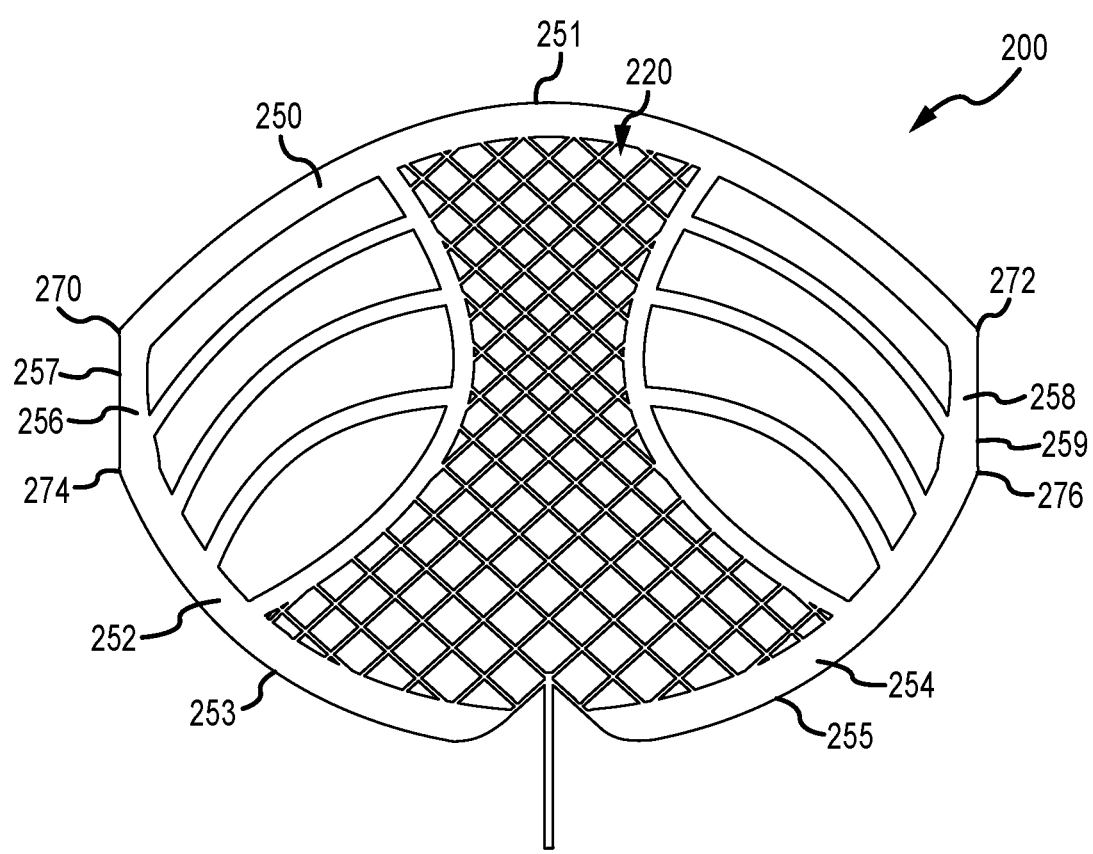
Figure 16C:
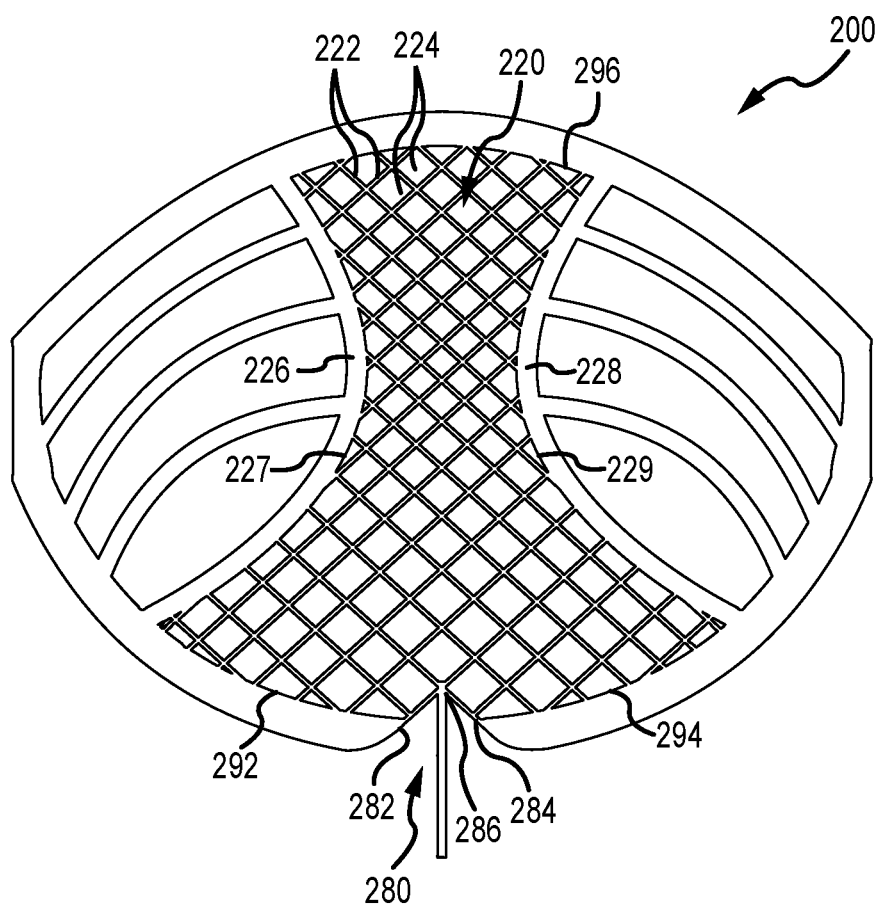

In another embodiment, and referring now to FIGS. 16a-16c, a graticulate support member (200) comprises an outer perimeter (210), a graticulate matrix portion (220), and one or more support arms (230) extending from the outer perimeter (210) to the graticulate matrix portion (220). The one or more support arms (230) define gaps (234) disposed between the outer perimeter (210) and the graticulate matrix portion (220). This embodiment may be useful, for instance, where ease of manufacturability and/or less materials are required to produce an acceptable support member.

In the illustrated embodiment, the outer perimeter (210) comprises a top portion (250), a left bottom portion (252), a right bottom portion (254), a left side portion (256) and a right side portion (258). The left and right bottom portions (252, 254) are separated by an optional lower gap (280), which is in the form of a notch in the outer perimeter (210). The optional lower gap (280) is partially defined by a first lower edge portion (282) and a second lower edge portion (284). The first and second lower edge portions (282, 284) convene at an apex (286). The first and second lower edges (282, 284) partially define the outer perimeter (210). The optional lower gap (280) may facilitate, for instance, flexing of the graticulate support member (200). In other embodiments, this gap is absent and a continuous bottom portion is used (see, e.g., FIG. 11A).

The top portion (250) of the outer perimeter (210) may include an arcuate outer edge (251). In the illustrated embodiment, the top portion (250) is connected to the left side portion (256) and the right side portion (258). The top portion (250) transitions to left side portion (256) at a first transition point (270), and the top portion (250) transitions to the right side portion (258) at a second transition point (272). The left side portion (256) may include a planar face (257). Likewise, the right side portion (258) may include a planar face (259). Use of a planar face may facilitate, for instance, production of the graticulate support member (200) by the CLIP'ing version of additive manufacturing. The left side portion (256) may transition to the left bottom portion (252) at a third transition point (274). The right side portion (258) may transition to the right bottom portion at a fourth transition point (276). The bottom left portion (252) may include an arcuate outer edge (253). Likewise, the bottom right portion (253) may include an arcuate outer edge (255).

In the illustrated embodiment, the graticulate support member (200) comprises a graticulate matrix portion (220). The graticulate matrix portion (220) is disposed between the top portion (250) and the bottom portion(s) (252, 254) of the outer perimeter (210). The graticulate matrix portion (220) generally comprises a first longitudinal side (rib) (226) and an opposing second longitudinal side (rib) (228). The first longitudinal side (226) is located inside the outer perimeter (210) and generally extends from the top portion (250) to the left bottom portion (252) of the outer perimeter (210). In the illustrated embodiment, the first longitudinal side (226) has a generally concave shape (e.g., a crescent shape). The second longitudinal side (228) is also located inside the outer perimeter (210) and generally extends from the top portion (250) to the right bottom portion (254) of the outer perimeter (210). In the illustrated embodiment, the second longitudinal side (226) has a generally concave shape. In the illustrated embodiment, the graticulate matrix portion (220) is symmetrical about it vertical axis, but is asymmetrical about is horizontal axis. In the illustrated embodiment, an upper portion of the graticulate matrix (220) comprises a first width (W1), a middle portion comprises a second width (W2) and a lower portion comprises a third width (W3), wherein W2<W1<W3. The graticulate matrix portion (220) may thus comprise a decanter-like shape and/or an hourglass-like shape. Such a shape may be useful, for instance, when the graticulate support member (200) is used in a brassiere.

One or more of the support arms (230) may extend from the first longitudinal side (226) to the left bottom portion (252). One or more of the support arms (230) may extend from the first longitudinal side (226) to the left side portion (256). One or more of the support arms (230) may extend from the second longitudinal side (228) to the right bottom portion (254). One or more of the support arms (230) may extend from the second longitudinal side (228) to the right side portion (258).

Figure 17:
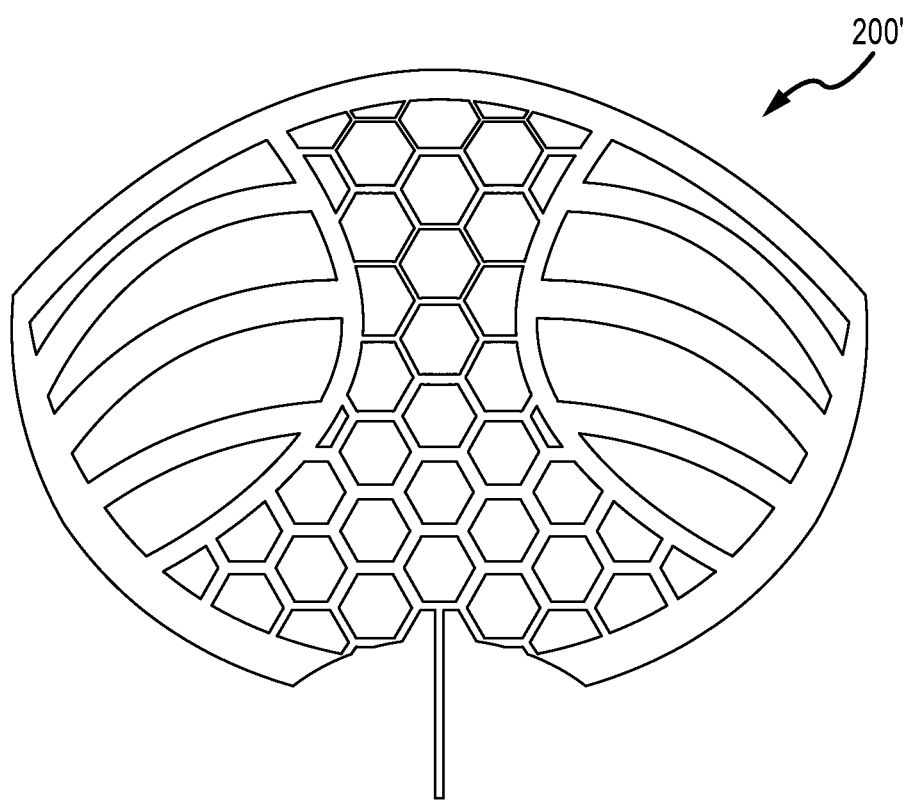
FIG. 17 is a top view of another embodiment of a graticulate support member having an inner graticulate support matrix portion, wherein the graticulate support matrix portion is generally honeycomb shaped.
Figure 18:
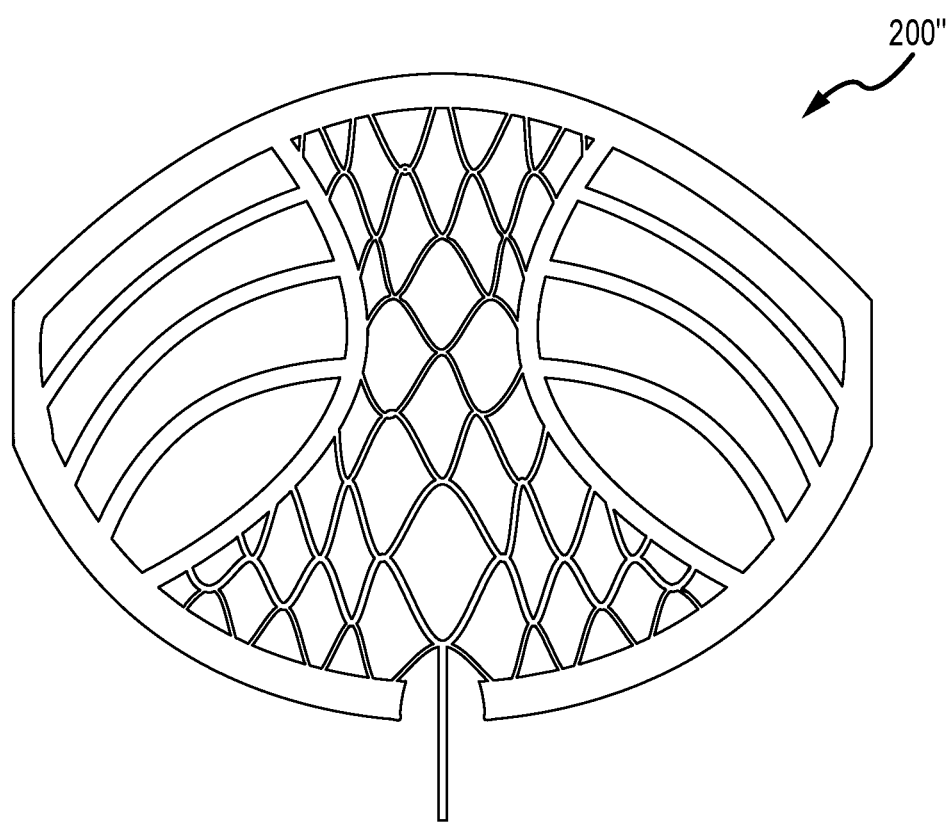
FIG. 18 is a top view of another embodiment of a graticulate support member having an inner graticulate support matrix portion, wherein the graticulate support matrix portion is ellipsoidal shaped.

The graticulate matrix portion (220) generally comprises a plurality of interlacing members (222) which define a plurality voids (224). The interlacing members may be any of the interlacing members described herein, e.g., may be linear or non-linear, and thus may define rectangular, square, ovular or circular shaped voids (224). This is shown for instance, in FIGS. 17-18. In FIG. 17, a graticulate support member 200' includes a plurality of interlacing members in a generally honeycomb configuration and define a plurality of generally hexagonal shaped voids or partial hexagonal shaped voids. In FIG. 18, a graticulate support member 200" includes a plurality of interlacing members in a generally sinusoidal-like configuration and define a plurality of generally ellipsoidal shaped voids or partial ellipsoidal shaped voids.

As previously described, the interlacing members may also have varying lengths, widths and/or thicknesses. One embodiment of this is shown in FIG. 17, wherein the interlacing members located proximal the bottom of the graticulate support member 200' have a larger width than the interlacing members located proximal the top of the graticulate support member 200". Thus, at least some of the interlacing members may define a first geometrical shape having a first perimeter, while others of the interlacing members may define a second geometrical shape having a second perimeter. In one embodiment, the first geometrical shape is the same as the second geometrical shape. In another embodiment, the first geometrical shape is different than the second geometrical shape. In one embodiment, the first perimeter has a first thickness and the second perimeter has a second thickness. In one embodiment, the first thickness is different than the second thickness. In one embodiment, the first thickness is uniform. In one embodiment, the first thickness is non-uniform. In one embodiment, the second thickness is uniform. In one embodiment, the second thickness is non-uniform.

Referring back to FIG. 15, various portions of the graticulate support member (200) may comprise a variable thickness. In the illustrated embodiment, the graticulate matrix (220) comprises a variable thickness and the support members (230) comprise a variable thickness, while the outer perimeter (210) comprises a generally uniform thickness. In one embodiment, the outer perimeter (210) comprises a variable thickness. In one embodiment, the graticulate matrix portion (220) comprises a uniform thickness while the support members (230) and/or outer perimeter (210) comprise a variable thickness. In another embodiment, the support members (230) comprise a uniform thickness while the graticulate matrix portion (220) and/or the outer perimeter comprises a variable thickness. In another embodiment, the outer perimeter (210) comprises a generally uniform thickness while the support members (230) and/or graticulate matrix portion (220) comprise a variable thickness.

In one embodiment, the average thickness of the graticulate matrix portion (220) is larger than (a) the average thickness of the support members (230), (b) the average thickness of the outer perimeter (210), or (c) the average thicknesses of both the support members (230) and the outer perimeter (210). In some of these embodiments, the average thickness of the support members (230) is larger than the average thickness of the outer perimeter (210). In others of these embodiments, the average thickness of the support members (230) is smaller than the average thickness of the outer perimeter (210). In yet others of these embodiments, the average thickness of the support members (230) is the same as the average thickness of the outer perimeter (210).

In another embodiment, the average thickness of the outer perimeter (210) is larger than (a) the average thickness of the support members (230), (b) the average thickness of the graticulate matrix portion (220), or (c) the average thicknesses of both the support members (230) and the graticulate matrix portion (220). In some of these embodiments, the average thickness of the support members (230) is larger than the average thickness of the graticulate matrix portion (220). In some of these embodiments, the average thickness of the support members (230) is smaller than the average thickness of the graticulate matrix portion (220). In some of these embodiments, the average thickness of the support members (230) the same as the average thickness of the graticulate matrix portion (220).

In another embodiment, the average thickness of the support members (230) is larger than (a) the average thickness of the outer perimeter (210), (b) the average thickness of the graticulate matrix portion (220), or (c) the average thicknesses of both the outer perimeter (210) and the graticulate matrix portion (220). In some of these embodiments, the average thickness of the outer perimeter (210) is larger than the average thickness of the graticulate matrix portion (220). In others of these embodiments, the average thickness of the outer perimeter (210) is smaller than the average thickness of the graticulate matrix portion (220). In others of these embodiments, the average thickness of the outer perimeter (210) is the same as the average thickness of the graticulate matrix portion (220).

Referring back to FIGS. 16a-16c, at least some of the interlacing members (222) are generally connected to and disposed between the first and second longitudinal sides (226, 228). In the illustrated embodiment, at least some of the interlacing members (222) connect to the arcuate faces (227, 229) of the first and second longitudinal sides (226, 228), respectively. In the illustrate embodiment, at least some of the interlacing members (222) connect to the top portion (250) of the outer perimeter (210), such as at inner arcuate edge (296). In the illustrate embodiment, at least some of the interlacing members (222) connect to the bottom portion(s) (252, 254) of the outer perimeter (210), such as at inner arcuate edges (292, 294).

The graticulate support member (200) may comprise an optional positioning arm (240). In the illustrated embodiment, the optional positioning arm (240) extends from the outer perimeter (210) and away from the graticulate matrix portion (220). In the illustrated embodiment, the positioning arm (240) is partially located within the gap (280) (notch) associated with the outer perimeter (210). In other embodiments, the positioning arm (240) may be completely located within the gap (280) (notch) associated with the outer perimeter (210). In other embodiments, such as when the optional gap (280) is absent, the positioning arm (240) may extend from an outer edge of the outer perimeter (210)

The positioning arm (240) may be used, for instance, to facilitate positioning of the graticulate support member (200) within a garment (e.g., positioning within a pocket of a garment). Once positioned within the garment, the positioning arm (240) may be removed from the graticulate support member (200), such as by fatiguing a joint associated with the positioning arm (240) (e.g., a joint located at or proximal to the apex (286)) and/or by severing the positioning arm (240) (e.g., by cutting). In another embodiment, the positioning arm (240) is used to position the graticulate support member (200) between at least one of the inner and outer cups (not illustrated). When a forging operation is used, a die or mandrel may sever the positioning arm (240) during or concomitant to the forging operation.

In the illustrated embodiment of FIGS. 16a-16c, the first and second side portions (256, 258) are included. In other embodiments, one or both of these side portions may be omitted. Thus, in some embodiments, the graticulate support member (200) may comprise a generally eye-shaped outer perimeter (210) (see, e.g., FIG. 17).

Manufacture of Breast Cups

As described above, a first cup cover (50) may be disposed to underlie the support member (20), and a second cup cover (52) is disposed to overlie the support member (20).

In forging embodiments, once positioned appropriately, a cup (100) may be formed by application of heat and force to mold the cup (100) Forming the cup (100) may further comprise applying an adhesive between the first cup and second cup prior to forming. In one embodiment, an adhesive is a corn-starch type adhesive. In one embodiment, the adhesive is a natural corn-starch type adhesive. In other embodiments, a graticulate support member may be inserted into a pocket of the brassiere. The pocket may be at least partially defined by the first cup cover (50) and the second cup cover (52).

The first cup cover (50) and second cup cover (52) may be manufactured from a material suitable for direct contact with a wearer's breast(s). When used as part of the pocket, conventional fabrics may be used for the first cup cover (50) and/or second cup cover (52). When forging steps are used, the cup cover materials may include, for instance, foams such as synthetic and natural materials. Synthetic materials may include polymer-based materials such as polyurethane, polyester, lycra (polyurethane and polyester copolymer commonly referred to as spandex). Natural materials may include an all-natural corn starch foam, an all-natural corn starch and sugar blend, or hemp, and combinations thereof. In one embodiment, the first cup cover (50) and/or second cup cover (52) is made from polyurethane foam. In another embodiment, the first cup cover (50) and or second cup cover (52) is made from an all-natural corn starch foam. In another embodiment, the first cup cover (50) and/or second cup cover (52) is made from an all-natural corn starch and sugar blend. In another embodiment, the first cup cover (50) and/or second cup cover (52) is made from polyester. In yet another embodiment, the first cup cover (50) and/or second cup cover (52) is made from a blend of polyester and polyurethane.

In another aspect, one of the first and second cup covers is produced by additive manufacturing. For instance, during production of the graticulate support member, the first and/or second cup covers may also be additively manufactured, thus producing an integral graticulate support member and cup cover(s) arrangement. In another embodiment, the first and/or second cup covers may be additively manufactured separate from the graticulate support member. The cup cover(s) may comprise a first polymeric material having first properties, and the graticulate support member may comprise a second polymeric material, different than the second polymeric material and therefore having second properties. Using different polymers and properties may facilitate an improved combination of properties. For instance, an improved combination of at least two of comfort, breathability and support may be realized (e.g., when a first polymer is more comfortable/soft and/or more "breathable" than the second polymer, but the second polymer is more rigid than the first polymer.)

Biometrics

The characteristics and methods of manufacture of the new support members (20) may allow the new support members (20) to act as a substrate. For instance, the new support members (20) may act as a substrate for one or more biometric sensors. Biometric sensors may, for instance, be incorporated into the new support members (20) by additive manufacturing. In one embodiment, the method of incorporating a biometric sensor into a support member (20) comprises (a) placing a biometric sensor into the matrix after at least some portion of the support member (20) has been manufactured, and (b) manufacturing one or more other portions of the support member (20) (e.g., manufacturing the remainder of the support member), thereby embedding the biometric sensor, where both sides of the biometric sensor are enclosed by the support member (20). In another embodiment, the method of incorporating a biometric sensor into a support member (20) comprises additively manufacturing the support member (20) onto one or more biometric sensors, thereby partially enclosing the biometric sensor. Another method may, for instance, include stitching (e.g., weaving) the biometric sensor into the support member (20). In one embodiment, the method of incorporating a biometric sensor into a support member (20) comprises stitching the biometric sensor, wherein the stitching includes, (a) modifying one or more biometric sensors to include threading holes, and (b) threading the threading holes with a needle and a thread, thereby attaching the one or more biometric sensors to the support member (20). The methods of incorporating one or biometric sensors may be applied such that the one or more biometric sensors are located adjacent to the inner cup cover (52), or adjustment to the outer cup cover (50), and combinations thereof.

As described above, the new support members (20) may have one or more biometric sensors incorporated therein. The new support members (20) having such incorporated biometric sensor(s) may be used for production of biometric data. For instance, one or more incorporated biometric sensors may produce biometric data by monitoring a vital sign. Some non-limiting examples of vital signs which may be monitored include body temperature, pulse (heart rate), respiration rate (breathing rate), and or blood pressure.

A support member (20) having incorporated one or more biometric sensors may produce biometric data by electrophysiological signals. Some non-limiting examples of electrophysiological signals which may be monitored include electrocardiographic signals (electrical activity of a heart), and electromyographic signals (electrical activity of muscle tissue(s)).

In one approach, the new support members (20) having such incorporated biometric sensor(s) may produce data concerning a condition. An example of a condition which may be monitored may be diabetes (e.g., by measuring blood glucose levels; insulin levels). Another example of a condition which may be monitored is sleep apnea, which may be measured by pulse oximetry (the measure of oxygen saturation in the blood). In yet another example, a wearer may monitor the condition of pregnancy by detecting contractions of the uterine muscles. In yet another example, a wearer may monitor the condition of breast milk contained by the breast (e.g., to determine the appropriate time to breast-feed a baby, or in determining how much milk is consumed during breast-feeding). In another example, a wearer may monitor a condition of frostbite exposure, such as by monitoring both moisture content and temperature. In yet another example, a wearer may monitor a condition of a menstrual cycle, by monitoring basal body temperature (e.g., a temperature of the body when at rest), in which ovulation periods and menstruation periods may be detected.

In one approach, the new support members (20) having such incorporated biometric sensor(s) may produce data concerning an infection or disease. A non-limiting example of disease which may be monitored may be cancer (e.g., monitoring tumor growth), by measuring blood flow (e.g., by a thermal conductivity measurement), by tracing cancer biomarkers (e.g., by measuring alpha-fetoprotein (AFP)), and/or by measuring heat distribution (e.g., via infrared radiation). An example of an infection which may be monitored includes viral and/or bacterial infections (e.g., monitoring a fever by body temperature; monitoring white blood cell count with pulse oximetry).

In another approach, the new support members (20) having such incorporated biometric sensor(s) may be used in the production of environmental data. A few non-limiting examples of environmental data which may be monitored include pollution data (e.g., pollution compounds concentrations found in the atmosphere such as ozone, carbon monoxide, $NO_x$ compounds, and $SO_x$ compounds), or harmful gases data which may be found in a dangerous work environment (e.g., concentrations of hydrogen sulfide, carbon monoxide, hydrocarbon gases, $SO_x$, and $NO_x$). Another non-limiting example of environmental data which may be monitored includes pollen levels, which may be useful for a wearer with allergies.

The new support members (20) may have at least two incorporated biometric sensors. For instance, at least two different categories (e.g., a vital sign, electrophysiological signal, a condition, an infection, a disease, or environmental data) and variations within a category (e.g., measuring both body temperature and pulse, which are vital signs) of biometric data may be measured either in one or more cups (100). For example, it may be preferable to place at least two biometric sensors in a single cup (100) of a brassiere (10) or other garment, such that the biometric sensors may be located adjacent to additional components (e.g., a transmittal device; a battery). Additionally, at least two different categories of biometric data, for example a condition and environmental data, among many others, may be measured in separate cups (100). Furthermore, at least two incorporated biometric sensors may be placed into a single cup, which may produce data of a single variation. For instance, a wearer may monitor for breast cancer developments, by incorporating an array of biometric sensors into a support member (20). Additionally, at last two incorporated biometric sensors may be placed in separate cups, which may produce data of a single variation. One or more biometric sensors placed in a first cup may be interconnected (e.g., by components such as wires, batteries, transmittal device) to one or more biometric sensors placed in a second cup. An example array of biometric sensors may produce three dimensional data which measures the blood flow (e.g., by thermal conductivity measurement), which may consequently diagnose the presence of breast cancer, as well as an approximate location of the diagnosed breast cancer (e.g., due to blood flow changes). For instance, for those who have undergone previous cancer treatments (e.g., radiation, lumpectomy, mastectomy), one or more biometric sensors could be used in one or more cups of the garments described herein to detect biometrics associated with a potential reoccurrence of the cancer. In the case of a lumpectomy or mastectomy, one or more biometric sensors could be used in combination with a restorative piece or pieces, and with the garments described herein, to detect biometrics associated with a potential reoccurrence of the cancer.

As may be appreciated, one or more biometric sensors described above may also be incorporated into a breast cup (100), for instance, into the inner cup cover (52). Incorporating the one or more biometric sensors into an inner cup cover (52) may allow for skin contact (e.g., with the biometric sensor(s) with the breast of a wearer), which may allow for certain biometric data to be collected (e.g., electrophysiological signals). Further, skin contact with the biometric sensor(s) may allow for certain biometric data to be collected with greater accuracy and precision. Skin contact with the breast of a wearer may be realized by incorporating one or more biometric sensors into a support member (20). For instance, a cup (100) having the support member (20) enclosed by an outer cup cover (50) and an inner cup cover (52), may have at least some portion of the inner cup cover (52) removed (e.g., a portion consistent with the size and location of a biometric sensor), exposing the one or more biometric sensors to the skin of a wearer.

Various combinations of cups having incorporated biometric sensors may be produced. The one or more biometric sensors may be placed in one or more cups (100). The one or more biometric sensors may be incorporated by various methods, such as, by additively manufacturing the biometric sensor into a support member (20) (e.g., embedding the biometric sensor), or by stitching (e.g. weaving) the biometric sensor into a support member (20), and combinations thereof. The one or more biometric sensors may produce data of one or more categories (e.g., a condition and environmental data, among many other combinations), and of one or more variations (e.g., a variation of body temperature of the vital sign category) as described above, and combinations thereof. The one or more biometric sensors may be used for producing data for one or more purposes other than described above. For instance, pulse oximetry may be useful in more than monitoring sleep apnea or detecting infection, and may be used to monitor both sleep apnea and infection. The one or more biometric sensors may be interconnected, and may be interconnected in one or more cups, and combinations thereof. The one or more biometric sensors may be located adjacent the inner cup cover (52), adjacent the outer cup cover (50), and combinations thereof.

Support members (20) incorporating one or more biometric sensors may be utilized along with a transmittal device and a transmittal method to transmit continuous and/or discrete data to a receiving device. The data may be received by a receiving device of the wearer or of a third party (e.g., a doctor monitoring a wearer's health condition), and combinations thereof. The receiving device may utilize an application which may analyze, store, and organize the data. Non-limiting examples of receiving devices may be a smartphone and a computer, among others. Transmittal methods may be wireless or wired, and combinations thereof. Wireless transmittal methods may include Bluetooth, cellular, or a wireless communication standard (e.g., an 802.11 standard as defined by the IEEE (Institute of Electrical and Electronics Engineers), and combinations thereof. Wired transmittal methods may include utilizing a twisted-pair wire, a coaxial cable, or a fiber-optic cable, and combinations thereof.

Post-Surgery, Recovery Brassiere

As described above, the new breast cups (100) may be useful for a wearer who has undergone an operation (e.g., augmentation, lumpectomy, mastectomy, or double-mastectomy). After receiving an operation, a wearer may undergo a period of recovery. Recovery period brassieres or other garments (10) may comprise a recovery period material in the cup(s) (100) or other components, which may aid in supporting the breast(s) (e.g., by compression) and or by reducing susceptibility to infection in order to promote healing of the breast(s). A recovery period brassiere or other garment may be absent of an underwire. Recovery period materials may include nylon, lycra (spandex), and combinations thereof. The recovery period brassiere or other garment may also be an F5 certified compression garment.

3D Imaging for Post-Operative Individuals

As described above, the new breast cups (100) may be useful for a wearer who has undergone an operation (e.g., augmentation, lumpectomy, mastectomy, or double-mastectomy). After recovery from a partial (e.g., lumpectomy) or whole (e.g., mastectomy) breast(s) removal operation, a wearer may experience a psychological reaction due to the new appearance of the breast(s). A brassiere or other garment may restore the pre-operative appearance of the breast(s), which may decrease the psychological effect. As described above, formation of breast cups (100) devised for wear by a particular user may be shaped to accommodate the unique anatomy of a wearer. The unique anatomy of a wearer may be recorded by 3D image capture prior to breast(s) surgery. For example, for an individual undergoing breast(s) surgery, for medical purposes, may have 3D image capture performed prior to an operation. The anatomy of negative volume created by breast(s) surgery of a wearer may be rendered by using the 3D image data collected prior to operation and 3D imaging data collected subsequent to the operation. For example, a digital profile may be produced by calculating the difference between the 3D image data subsequent and the 3D image data prior to the operation. Additionally, a digital profile of a breast, absent of 3D imaging data collected prior to operation, may be created by using a mirror image of an un-altered breast. The negative volume may be rendered digitally, creating a digital profile, which may be produced using additive manufacturing, to create a restorative volume piece or pieces. The restorative volume piece(s) may be incorporated into breast cup(s) (100) having the support member(s) (20), thereby restoring the pre-operative appearance of the breast(s), and alleviating the psychological effect of the new appearance.

The restorative volume piece(s) may be incorporated into the breast cups (100). In one approach, the restorative volume piece(s) may be stitched (e.g., woven) into the second cup cover (52) (the inner cup cover contacting the breast). In another approach, the restorative volume piece(s) may be enclosed between a custom first cup cover (50) and a custom second cup cover (52). Enclosure of the restorative volume piece(s) between a custom first cup cover (50) and a custom second cup cover (52) may optionally include utilizing a custom mandrel (62) and custom mold (60) to forge the cup (100). In another approach, the new support members (20) may act as a substrate for printing a restorative volume piece or pieces, of which may be enclosed by a first cup cover (50) and a second cup cover (52) as described above. For instance, the voids (37) of a graticulate matrix (30) may be suitable structures to additively manufacture restorative volume pieces. The restorative volume piece or pieces may be enclosed within a cup (100), adjacent to the inner cup cover (52) or the outer cup cover (50), and combinations thereof. In other embodiments, any one cup (100) may be manufactured with a restorative volume piece or pieces and absent of a support member (20). For instance, a woman who has undergone a mastectomy may wear a brassiere (10) where one cup (100) comprises a restorative volume piece in the dimensions of the removed breast, and another cup (100) of design.

The restorative volume piece(s) may be manufactured from materials which may enhance the comfort and appearance for the wearer. For instance, the restorative volume piece(s) may be additively manufactured from a material, or multiple materials, having differing densities and potentially other physical properties. Manufacture of the restorative volume piece(s) from multiple materials may allow for customization of the manufactured brassiere or other garment, which imitates the weight and feel of the pre-operative breast(s). Materials which may be used for manufacture of the restorative volume piece(s) may include, thermoplastics, elastomers, thermoplastic elastomers, and combinations thereof. The material may also be in the form of a foam or gel, among others. In one embodiment, the one or more materials is a thermoplastic elastomer comprising polyurethane. In another embodiment, the one or more materials is a thermoplastic elastomer comprising Nylon-6. In another embodiment, the one or more materials is a thermoplastic elastomer. In another embodiment, the one or more materials is an elastomer comprising a silicone gel. In another embodiment, the one or more materials is a gel comprising a hydrogel.

Breast cup(s) (100) may be produced with a support member (20) having incorporated a restorative volume piece or pieces. In some embodiments, the shape of the restorative volume piece or pieces may resemble a whole breast, for instance, in the case of a wearer who has undergone a mastectomy or double-mastectomy. In these embodiments, the cup (100) may be produced by a method in which the inner cup cover (52) is not volumetrically domed, but is generally planar, in order to rest comfortably against a wearer's chest, where the breast has been removed by mastectomy.

Custom breast cups (100) may also be entirely additively manufactured. For instance, the first cup cover (50) and second cup cover (52), and support member (20), may be additively manufactured in the final shape of a volumetrically domed breast cup. Volumetrically domed first cup covers (50), second cup covers (52), and support members (20) may be realized, or the entire breast cup (100) may be additively manufactured as one continuous body. Additive manufacturing of breast cup(s) (100), therefore, obviates the need for a custom mandrel (62) or mold (60) to produce a custom breast cup (100).

Modified Cup Shape for Breast Augmentations

Figure 13:
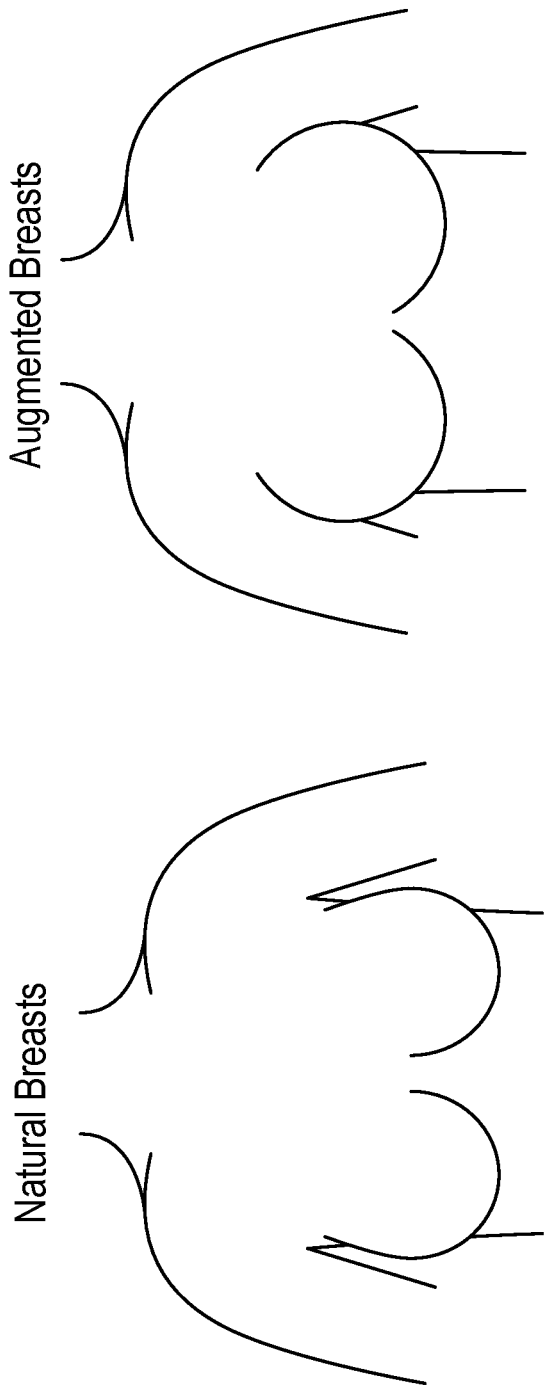
FIG. 13 is a frontal view of a pair natural breasts versus a pair of augmented breasts.
Figure 14:
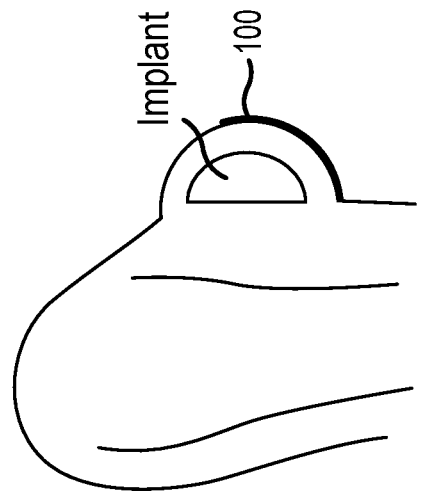
FIG. 14 is a side view of a pair of natural breasts versus augmented breasts, with cups (100) for each type shown.

A breast cup (100) in a conventional brassiere or garment may be designed to support the weight of the breast, by supporting the bottommost portion of the breast (e.g., with an underwire). A wearer who has undergone an operation such as a breast augmentation (e.g., received breast implants) may have more spherical breasts than natural breasts, as seen in FIGS. 13 and 14. Supporting spherical implants in an augmented breast with an underwire may result in movement of the implants, as well as reducing the speed of recovery after a surgery. A breast cup (100) comprising an appropriately sized and/or shaped support member (20) and/or appropriately sized and/or shaped inner and/or outer cups (50, 52) may prevent movement of the implants, and may enhance the speed of recovery.

Custom Mold and Mandrel

As described above, formation of particular breast cups (100) devised for wear by a particular user (e.g., customized breast cup(s)), having the new support members (20) incorporated therein are considered in the present disclosure. Forming customized breast cups (100) may optionally comprise (see FIG. 9) producing a custom mold (60) and or custom mandrel (62) prior to forging the appropriate doming. At least a portion of the mandrel (62) may be customized to represent a particular wearer's anatomy upon forging. A customized mandrel (62) may comprise a non-customized mandrel (62), having a customized portion attached by some attaching means. The customized mandrel (62) or customized portion of the mandrel (62) may be produced by additive manufacturing, where 3D imaging data is utilized in manufacturing in a similar fashion to restorative volume pieces, as described above. Similarly, a custom mold (60) or at least some portion of a customized mold (60) may be produced in the same fashion as the customized mandrel (62).

As may be appreciated, each wearer may have unique breast dimensions, which may not be represented by conventional brassieres and other garments. Custom molds (60) and corresponding mandrels (62) may be manufactured for each individual wearer, which may be considered impractical. However, a limited set of molds (60) and mandrels (62) representing, for example, 12 different breast shapes, and the corresponding cup (100) sizes, may be a practical approach to customizing breast cups (100).

Combinations of Bra Cups

Brassieres and other garments may be produced using various combinations of the above embodiments. For instance, any one cup (100) may include one or more graticulate support members (20), or include a restorative volume piece or pieces. Further, any one cup (100) may be of a conventional cup design. In one embodiment, a brassiere or other garment comprises a first cup comprising one or more enclosed graticulate support members (20), and a second cup comprising a conventional breast cup design. In another embodiment, a brassiere or other garment comprises a first cup comprising one or more enclosed graticulate support members (20), and a second cup comprising a restorative volume piece or pieces. In another embodiment, a brassiere or other garment comprises a first cup and second cup, each comprising one or more enclosed graticulate support members (20).

OTHER USES

As noted above, the presently disclosed brassieres and garments may generally be for the purpose of supporting breasts, for example, the breasts of a male or female. In one embodiment, the brassiere or garment is for the purpose of covering one or more male breasts. In another embodiment, the brassiere or garment is for the purpose of covering one or more female breasts. Cups having a support member may be designed for other anatomical members, such as, for the purpose of covering, supporting, and or protecting the penis and testicles. A male cup, designed for the anatomical features of a penis and/or testicles may comprise a first cup cover, a second cup cover, and a support member, produced appropriately to cover the penis and/or testicles. For example, a male cup may be utilized in an athletic garment, in which the intended purpose may be to support and protect the penis and/or testicles of a wearer during a sporting activity (e.g., football, baseball, soccer, skiing, hockey, bicycling, running or other sporting exercise event). Another purpose may be for men's underwear, in which a male cup may be used to enhance the visual aesthetic of a penis and/or testicles within an undergarment. In one embodiment, a male cup comprising a first cup cover, a second cup cover, and a support member is used in athletic wear. In another embodiment, a male cup comprising a first cup cover, a second cup cover, and a support member is used to enhance the visual aesthetic of a penis and/or testicles within an undergarment. The male cups may include any of the biometric sensors described above. In one embodiment, a male garment comprises a sensor for detecting cancer (e.g., testicular cancer).

While various embodiments of the present disclosure have been described in detail, it is apparent that modifications and adaptations of those embodiments will occur to those skilled in the art. However, it is to be expressly understood that such modifications and adaptations are within the spirit and scope of the present disclosure.

What is claimed is:

1. A support apparatus for a garment, comprising:
    a polymer-based graticulate support member, wherein the polymer-based graticulate support member comprises:
    (a) an outer perimeter,
    (b) an angled arrangement of interlacing members within the outer perimeter, and
    (c) a plurality of voids at least partially defined by the interlacing members; and
    wherein a lower portion of the outer perimeter is at least partially defined by a rigid polymeric lower edge integral with ends of some of the interlacing members; and
    wherein at least the rigid polymeric lower edge is configured to provide support to a wearer of the garment.

2. The support apparatus of claim 1, wherein the outer perimeter of the polymer-based graticulate support member is in the shape of an eye, an anchor, or a cross.

3. The support apparatus of claim 1, wherein the polymer-based graticulate support member is non-symmetrical.

4. A brassiere incorporating the support apparatus of claim 1.

5. The support apparatus of claim 1, wherein the rigid polymeric lower edge is configured to be located proximal an inframammary fold of the wearer.

6. The support apparatus of claim 1, wherein the polymer-based graticulate support member comprises a uniform thickness.

7. The support apparatus of claim 1, wherein the polymer-based graticulate support member comprises a variable thickness.

8. The support apparatus of claim 7, wherein the variable thickness comprises one or more distinct sections of variable thickness.

9. The support apparatus of claim 7, wherein the variable thickness is a monotonic thickness gradient.

10. The support apparatus of claim 7, wherein the variable thickness is a non-monotonic thickness gradient.

11. The support apparatus of claim 7, wherein the variable thickness comprises a continuous thickness gradient.

12. The support apparatus of claim 11, wherein the continuous thickness gradient comprises a linear thickness gradient.

13. The support apparatus of claim 11, wherein the continuous thickness gradient comprises a non-linear thickness gradient.

14. The support apparatus of claim 7, wherein the variable thickness comprises a discontinuous thickness gradient.

15. The support apparatus of claim 7, wherein the variable thickness comprises a minimum thickness (Lt) and a maximum thickness (Mt), wherein a ratio of Lt to Mt is not greater than 0.90.

16. The support apparatus of claim 15, wherein the ratio of Lt to Mt is not greater than 0.75.

17. The support apparatus of claim 15, wherein the ratio of Lt to Mt is not greater than 0.50.

18. The support apparatus of claim 7, wherein the outer perimeter comprises at least one arcuate edge.

19. The support apparatus of claim 7, wherein the outer perimeter comprises at least one non-arcuate edge.

20. The support apparatus of claim 7, wherein the polymer-based graticulate support member is planar.

21. The support apparatus of claim 7, wherein the polymer-based graticulate support member is non-planar.

22. The support apparatus of claim 7, wherein the polymer-based graticulate support member comprises a glass transition temperature of at least 500° F.

23. The support apparatus of claim 7, wherein at least some of the plurality of voids define a parallelogram pattern.

24. The support apparatus of claim 7, wherein at least some of the plurality of voids define an ellipsoidal pattern.

25. The support apparatus of claim 7, wherein at least some of the plurality of voids define a triangular pattern.

26. The brassiere of claim 4, wherein the brassiere comprises a first cup cover adjacent the polymer-based graticulate support member.

27. The brassiere of claim 26, wherein the first cup cover comprises a material suitable for direct contact with a wearer's skin.

28. The brassiere of claim 27, wherein the first cup cover comprises synthetic materials.

29. The brassiere of claim 27, wherein the first cup cover comprises natural materials.

30. The brassiere of claim 26, wherein the polymer-based graticulate support member is disposed between the first cup cover and a second cup cover.

31. The brassiere of claim 30, wherein the first cup cover comprises a first material, wherein the second cup cover comprises a second material, wherein the first material is different than the second material.

* * * * *